(12) United States Patent
Coates et al.

(10) Patent No.: US 11,655,242 B2
(45) Date of Patent: May 23, 2023

(54) GLUCAGON-LIKE PEPTIDE1 RECEPTOR AGONISTS

(71) Applicant: Eli Lilly and Company, Indianapolis, IN (US)

(72) Inventors: David Andrew Coates, New Palestine, IN (US); Todd Fields, New Palestine, IN (US); Joseph Daniel Ho, San Diego, CA (US); Fucheng Qu, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 140 days.

(21) Appl. No.: 16/906,063

(22) Filed: Jun. 19, 2020

(65) Prior Publication Data
US 2020/0407347 A1 Dec. 31, 2020

Related U.S. Application Data

(60) Provisional application No. 62/904,906, filed on Sep. 24, 2019, provisional application No. 62/868,117, filed on Jun. 28, 2019.

(51) Int. Cl.
*C07D 405/14* (2006.01)
*A61P 3/10* (2006.01)
*A61K 9/00* (2006.01)

(52) U.S. Cl.
CPC .............. *C07D 405/14* (2013.01); *A61P 3/10* (2018.01); *A61K 9/0053* (2013.01)

(58) Field of Classification Search
CPC .................................................. C07D 405/14
See application file for complete search history.

(56) References Cited

U.S. PATENT DOCUMENTS

2020/0325121 A1* 10/2020 Zhong .................. C07D 471/04
2021/0171499 A1* 6/2021 Ammann ............. C07D 405/14

FOREIGN PATENT DOCUMENTS

| WO | 2018/109607 | 6/2018 |
|---|---|---|
| WO | 2019/239319 | 12/2019 |
| WO | 2019/239371 | 12/2019 |
| WO | 2020103815 A1 | 5/2020 |
| WO | 2020207474 A1 | 10/2020 |
| WO | 2021018023 A1 | 2/2021 |
| WO | 2021081207 A1 | 4/2021 |
| WO | 2021096284 A1 | 5/2021 |
| WO | 2021096304 A1 | 5/2021 |
| WO | 2021112538 A1 | 6/2021 |
| WO | 2021154796 A1 | 8/2021 |
| WO | 2021160127 A1 | 8/2021 |
| WO | 2021187886 A1 | 9/2021 |
| WO | 2021197464 A1 | 10/2021 |
| WO | 2021219019 A1 | 11/2021 |

OTHER PUBLICATIONS

Patent Cooperation Treaty International Search Report pertaining to International Application No. PCT/US2020/038617; International Filing Date: Jun. 19, 2020; dated Mar. 11, 2020.

Patent Cooperation Treaty Written Opinion of the International Searching Authority pertaining to International Application No. PCT/US2020/038617; International Filing Date: Jun. 19, 2020; dated Mar. 11, 2020.

* cited by examiner

*Primary Examiner* — Matthew P Coughlin
(74) *Attorney, Agent, or Firm* — Thomas Weber

(57) ABSTRACT

In an embodiment, the present invention provides a compound of the formula:

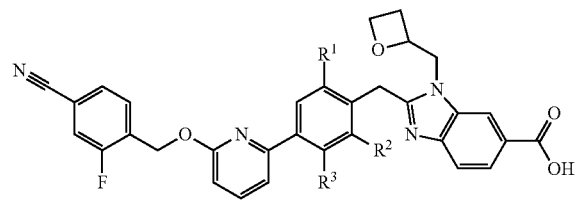

or a pharmaceutically acceptable salt thereof, and methods of using this compound for treating type II diabetes mellitus.

18 Claims, No Drawings

GLUCAGON-LIKE PEPTIDE1 RECEPTOR AGONISTS

This invention relates to glucagon-like peptide-1 receptor agonists and therapeutic uses of the compounds to treat type II diabetes mellitus.

Glucagon-like peptide-1 (GLP-1) is a member of the incretin family of peptide hormones secreted by intestinal enteroendocrine L-cells. GLP-1 induces the release of insulin from beta cells in a glucose dependent manner. However, GLP-1 is rapidly metabolized so that only a small percentage of the GLP-1 can be utilized to induce insulin secretion. To offset this, GLP-1 receptor (GLP-1R) agonists have been developed to enhance insulin secretion as a treatment for type II diabetes mellitus.

The majority of GLP-1R agonists that have been approved to treat type II diabetes mellitus are injectable agents. Patients often prefer orally administered drugs because of the drawbacks associated with injection such as inconvenience, pain, and the potential for injection site irritation.

WO2018/109607 discloses certain benzimidazole derivatives, which are described as GLP-1R agonists.

However, there is a need for alternative GLP-1R agonists. In particular, there is a need for GLP-1R agonists which can be administered orally. There is especially a need for GLP-1R agonists having improved potency, a favourable toxicology profile and/or a pharmacokinetic profile which supports once daily dosing.

Accordingly, the present invention provides a compound of the formula:

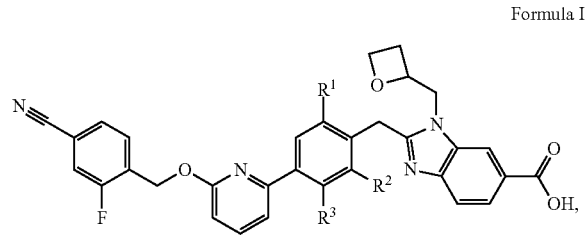

Formula I wherein
$R^1$ is H or F;
$R^2$ is H or F; and
$R^3$ is H or $CH_3$;
or a pharmaceutically acceptable salt thereof.

Formula I includes all individual enantiomers, and mixtures thereof, as well as racemates, and pharmaceutically acceptable salts thereof.

In an embodiment, there is a provided a compound of the formula:

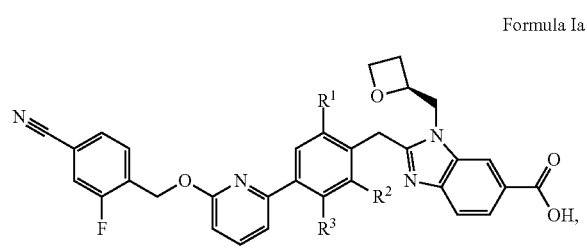

Formula Ia or a pharmaceutically acceptable salt thereof.

In an embodiment, there is provided a compound of the formula:

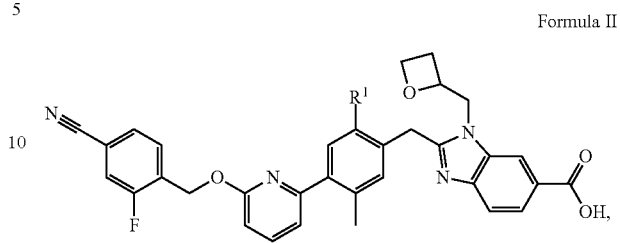

Formula II wherein $R^1$ is H or F, or a pharmaceutically acceptable salt thereof.

In an embodiment, there is provided a compound of the formula:

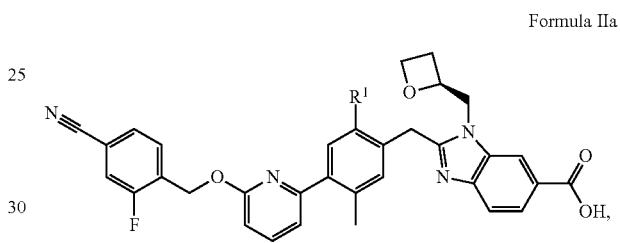

Formula IIa wherein $R^1$ is H or F, or a pharmaceutically acceptable salt thereof.

In one embodiment, the compound is a compound of the formula:

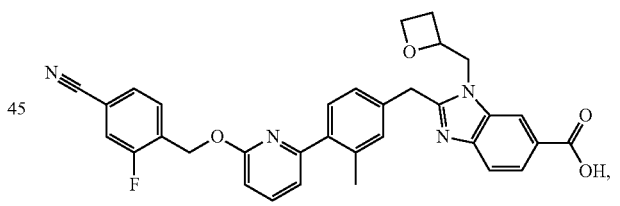

or a pharmaceutically acceptable salt thereof. In a preferred embodiment, the compound is a compound of the formula:

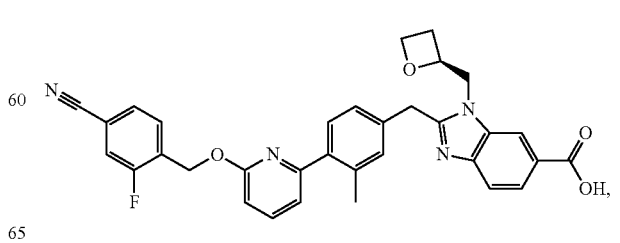

or a pharmaceutically acceptable salt thereof.

In one embodiment, the compound is a compound of the formula:

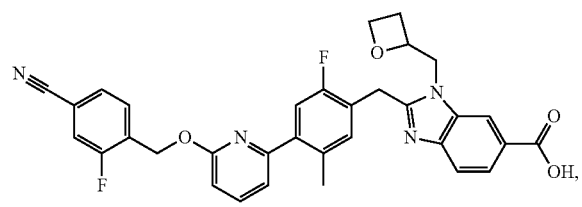 [SMILES: Cc1cc(Cc2nc3ccc(C(=O)O)cc3n2CC2CCO2)c(F)cc1-c1cccc(OCc2ccc(C#N)cc2F)n1]

or a pharmaceutically acceptable salt thereof. In a preferred embodiment, the compound is a compound of the formula:

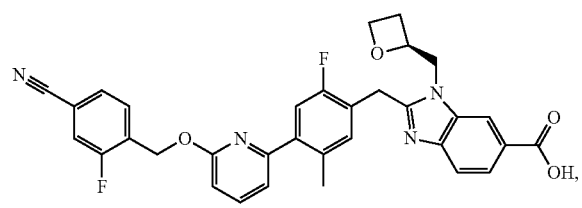 [SMILES: Cc1cc(Cc2nc3ccc(C(=O)O)cc3n2C[C@@H]2CCO2)c(F)cc1-c1cccc(OCc2ccc(C#N)cc2F)n1]

or a pharmaceutically acceptable salt thereof. In a particularly preferred embodiment, there is provided the tert-butylamine salt (also known as the erbumine salt) of:

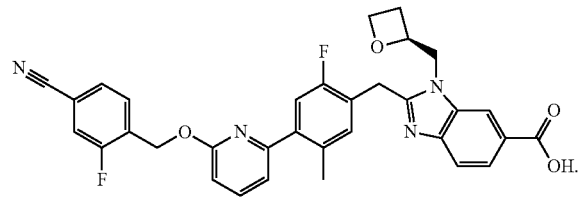

In an embodiment, there is provided a compound of the formula:

Formula III

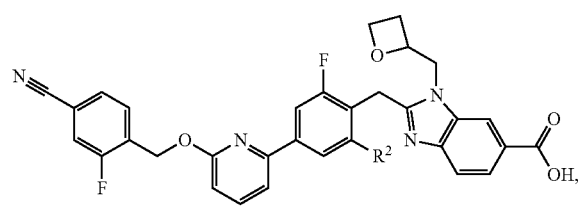

wherein R² is H or F, or a pharmaceutically acceptable salt thereof.

In an embodiment, there is provided a compound of the formula:

Formula IIIa

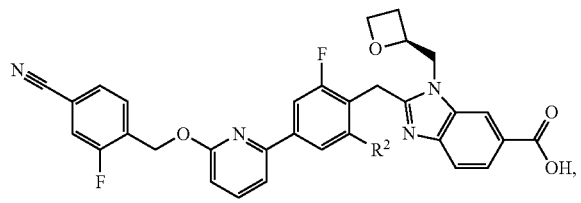

wherein R² is H or F, or a pharmaceutically acceptable salt thereof.

In one embodiment, the compound is a compound of the formula:

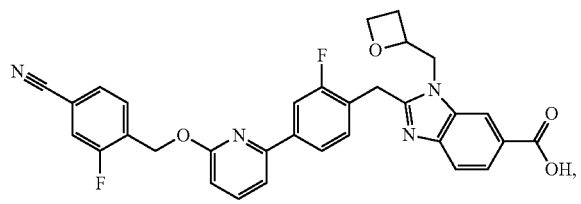

or a pharmaceutically acceptable salt thereof. In a preferred embodiment, the compound is a compound of the formula:

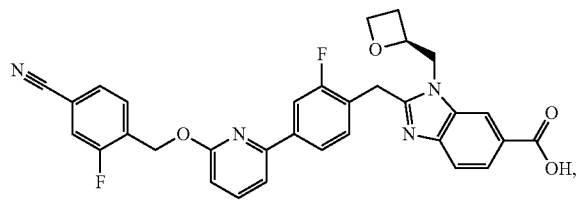 [SMILES: N#Cc1ccc(COc2cccc(-c3ccc(Cc4nc5ccc(C(=O)O)cc5n4C[C@@H]4CCO4)c(F)c3)n2)c(F)c1]

or a pharmaceutically acceptable salt thereof.

In one embodiment, the compound is a compound of the formula:

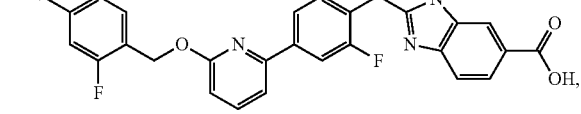

or a pharmaceutically acceptable salt thereof. In a preferred embodiment, the compound is a compound of the formula:

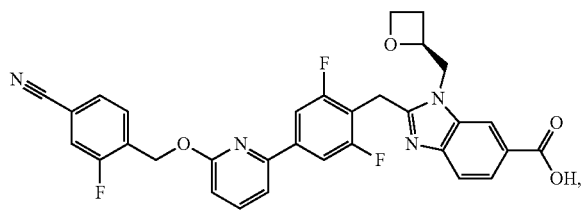

or a pharmaceutically acceptable salt thereof.

Formula I encompasses Formulae Ia, Ib, II, IIa, IIb, III, IIIa and IIIb and reference to Formula I below, for example in the methods of treatment and therapeutic uses, is also to be read as a reference to each and all of these sub-formulae.

In another embodiment, there is provided a pharmaceutically acceptable composition comprising a compound of Formula I, or a pharmaceutically acceptable salt thereof, and at least one of a pharmaceutically acceptable carrier, diluent or excipient. In a preferred embodiment, the pharmaceutically acceptable composition is formulated for oral administration.

In another embodiment, there is provided a method of treating a mammal for type II diabetes mellitus, the method comprises administering to the mammal in need of treatment a pharmaceutically acceptable composition comprising an effective amount of a compound of Formula I, or a pharmaceutically acceptable salt thereof, and at least one of a pharmaceutically acceptable carrier, diluent or excipient. In one embodiment, the pharmaceutically acceptable composition is formulated for oral administration. Preferably, the mammal is a human.

In another embodiment, there is provided a method of treating a mammal for type II diabetes mellitus, the method comprises administering to the mammal in need of treatment an effective amount of a compound of Formula I, or a pharmaceutically acceptable salt thereof. In a preferred embodiment, the mammal is a human.

In another embodiment, there is provided a method of lowering blood glucose levels in a mammal, the method comprises administering to the mammal in need of treatment an effective amount of a compound of Formula I, or a pharmaceutically acceptable salt thereof. In a preferred embodiment, the mammal is a human.

In another embodiment, there is provided a method of treating hyperglycemia in a mammal, the method comprises administering to the mammal in need of treatment an effective amount of a compound of Formula I, or a pharmaceutically acceptable salt thereof. In a preferred embodiment, the mammal is a human.

In an embodiment, there is provided a compound of Formula I, or a pharmaceutically acceptable salt thereof, for use in therapy.

In another embodiment, there is provided a compound of Formula I, or a pharmaceutically acceptable salt thereof, for use in the treatment of type II diabetes mellitus.

In another embodiment, there is provided a compound of Formula I, or a pharmaceutically acceptable salt thereof, for use in lowering blood glucose levels.

In another embodiment, there is also provided a compound of Formula I, or a pharmaceutically acceptable salt thereof, for use in treating hyperglycemia.

In an embodiment, there is provided the use of a compound of Formula I, or a pharmaceutically acceptable salt thereof, for the manufacture of a medicament for the treatment of type II diabetes mellitus.

In an embodiment, there is provided the use of a compound of Formula I, or a pharmaceutically acceptable salt thereof, for the manufacture of a medicament for lowering blood glucose levels.

In an embodiment, there is provided the use of a compound of Formula I, or a pharmaceutically acceptable salt thereof, for the manufacture of a medicament for the treatment of hyperglycemia.

In a preferred embodiment, the compound of Formula I is administered orally. In a preferred embodiment, the compound of Formula I is administered once daily. In another preferred embodiment, the therapeutic use is in a human.

The term "pharmaceutically acceptable salt" as used herein refers a salt of a compound of the invention considered to be acceptable for clinical and/or veterinary use.

Examples of pharmaceutically acceptable salts and common methodologies for preparing them can be found in "Handbook of Pharmaceutical Salts: Properties, Selection and Use" P. Stahl, et al., 2nd Revised Edition, Wiley-VCH, 2011 and S. M. Berge, et al., "Pharmaceutical Salts", *Journal of Pharmaceutical Sciences*, 1977, 66(1), 1-19.

Examples of pharmaceutical compositions and processes for their preparation can be found in "Remington: The Science and Practice of Pharmacy", Loyd, V., et al. Eds., $22^{nd}$ Ed., Mack Publishing Co., 2012. In one embodiment, the pharmaceutically compositions can be formulated for oral administration. Preferably the pharmaceutical compositions are formulated as a tablet, capsule, or a solution. The tablet, capsule, or solution can include a compound of Formula I in an amount effective for treating a patient in need of treatment.

The term "effective amount" refers to the amount or dose of a compound of Formula I, or a pharmaceutically acceptable salt thereof, which, upon single or multiple dose administration to the patient, provides the desired effect in the patient under diagnosis or treatment. The attending physician, as one skilled in the art, can readily determine an effective amount by the use of conventional techniques and by observing results obtained under analogous circumstances. Factors considered in the determination of an effective amount or dose of a compound include: whether the compound or its salt will be administered; the co-administration of other agents, if used; the species of mammal to be treated; its size, age, and general health; the degree of involvement or the severity of the disorder; the response of the individual mammal; the mode of administration; the bioavailability characteristics of the preparation administered; the dose regimen selected; and other relevant circumstances. The compounds of the present invention are effective at a dosage per day that falls within the range of about 0.01 to about 15 mg/kg of body weight.

As used herein, the terms "treating", "to treat", or "treatment", refers to lowering, reducing, or reversing the progression or severity of an existing symptom, disorder, or condition, such as hyperglycemia, which can include increasing insulin secretion.

The compounds of Formula I can be formulated as pharmaceutical compositions administered by any route which makes the compound bioavailable. Preferably, such compositions are for oral administration. Such pharmaceutical compositions and processes for preparing same are well known in the art (See, e.g., Remington, J. P., "Remington:

The Science and Practice of Pharmacy", L. V. Allen, Editor, 22nd Edition, Pharmaceutical Press, 2012).

The compounds of Formula I and the pharmaceutically acceptable salts thereof are useful in the therapeutic uses of the invention, with certain configurations being preferred.

Compounds of the present invention include:

Formula Ia

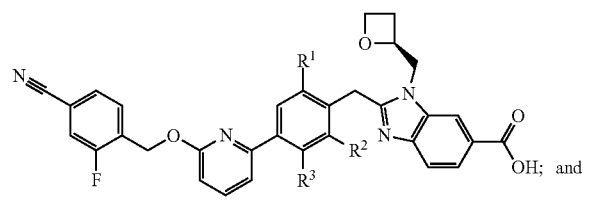

OH; and

Formula Ib

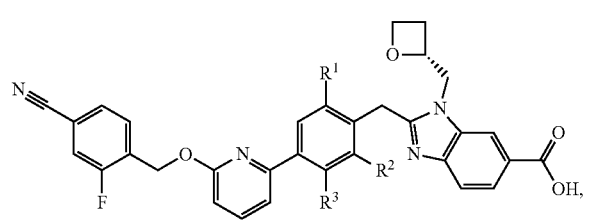

or pharmaceutically acceptable salts thereof.

Further compounds of the present invention include:

Formula IIa

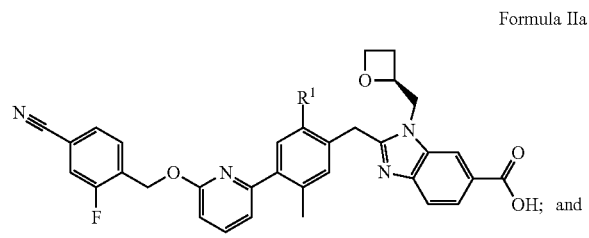

OH; and

Formula IIb

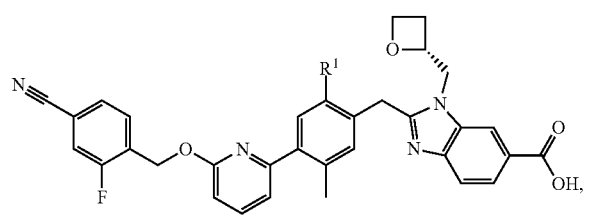 [SMILES: N#Cc1ccc(COc2cccc(-c3cc(F)c(Cc4nc5ccc(C(=O)O)cc5n4CC4CCO4)c(F)c3)n2)c(F)c1]

or pharmaceutically acceptable salts thereof.

Further compounds of the present invention include:

Formula IIIa

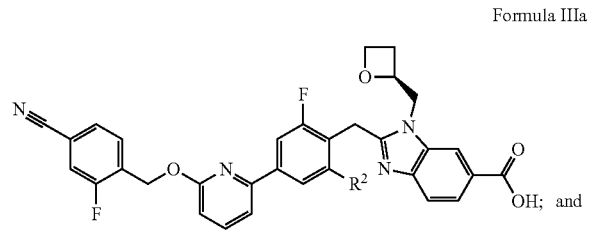

OH; and

Formula IIIb

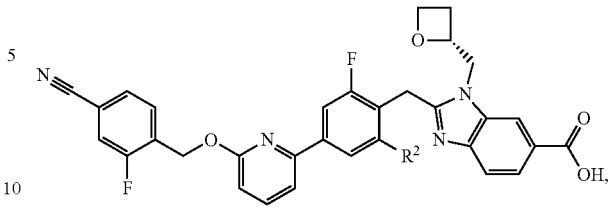

or pharmaceutically acceptable salts thereof.

Although the present invention contemplates all individual enantiomers, mixtures thereof, and racemates, compounds of Formula Ia, IIa and IIIa, and pharmaceutically acceptable salts thereof, are particularly preferred.

Individual enantiomers may be separated or resolved by one of ordinary skill in the art at any convenient point in the synthesis of compounds of the invention, by methods such as selective crystallization techniques, chiral chromatography (See for example, J. Jacques, et al., "*Enantiomers, Racemates, and Resolutions*", John Wiley and Sons, Inc., 1981, and E. L. Eliel and S. H. Wilen," *Stereochemistry of Organic Compounds*", Wiley-Interscience, 1994), or supercritical fluid chromatography (SFC) (See for example, T. A. Berger; "*Supercritical Fluid Chromatography Primer*," Agilent Technologies, July 2015).

A pharmaceutically acceptable salt of the compounds of the invention can be formed, for example, by reaction of a compound of Formula I and an appropriate pharmaceutically acceptable base in a suitable solvent under standard conditions well known in the art (See, for example, Bastin, R. J., et al.; *Org. Process. Res. Dev.*, 4, 427-435, 2000 and Berge, S. M., et al.; *J. Pharm. Sci.*, 66, 1-19, 1977). A preferred salt is the tert-butyl amine (or erbumine) salt.

Certain abbreviations used herein are defined according to Daub G. H., et al., "The Use of Acronyms in Organic Chemistry" *Aldrichimica Acta*, 1984, 17(1), 6-23. Certain abbreviations are defined as follows: "ACN" refers to acetonitrile; "ATP" refers to adenosine triphosphate; "BSA" refers to Bovine Serum Albumin; "cAMP" refers to cyclic adenosine-3',5'-monophosphate; "DCM" refers to dichloromethane or methylene chloride; "DIPEA" refers to N,N-diisopropylethylamine; "DMF" refers to N,N-dimethylformamide; "DMSO" refers to dimethyl sulfoxide; "$EC_{50}$" refers to the concentration of an agent which produces 50% response of the target activity compared to a predefined positive control compound (absolute $EC_{50}$); "ES/MS" refers to electrospray mass spectrometry; "EtOAc" refers to ethyl acetate; "HATU" refers to 1-[bis(dimethylamino)methylene]-1H-1,2,3-triazolo[4,5-b]pyridinium 3-oxide hexafluorophosphate; "HEK" refers to human embryonic kidney; "HEPES" refers to 4-(2-hydroxyethyl)-1-piperazineethanesulfonic acid; "h" refers to hours or hour, respectively; "MeOH" refers to methanol or methyl alcohol; "min" refers to minute or minutes; "Pd(dppf)Cl$_2$" refers to [1,1'-bis(diphenylphosphino)ferrocene]dichloropalladium(II); "RT" refers to room temperature; and "THF" refers to tetrahydrofuran.

The compounds of the present invention may be prepared by a variety of procedures, some of which are illustrated in the Preparations and Examples below. The specific synthetic steps for each of the routes described may be combined in different ways, to prepare compounds of the invention, or salts thereof. The product of each step below can be recovered by conventional methods, including extraction, evaporation, precipitation, chromatography, filtration, trituration, and crystallization. The reagents and starting materials are readily available to one of ordinary skill in the art. Individual isomers, enantiomers, and diastereomers may be separated or resolved at any convenient point in the synthesis, by methods such as, selective crystallization techniques or chiral chromatography (See for example, J. Jacques, et al., "*Enantiomers, Racemates, and Resolutions*", John Wiley and Sons, Inc., 1981, and E. L. Eliel and S. H. Wilen, "*Stereochemistry of Organic Compounds*", Wiley-Interscience, 1994). Without limiting the scope of the invention, the following preparations, and examples are provided to further illustrate the invention.

Scheme 1

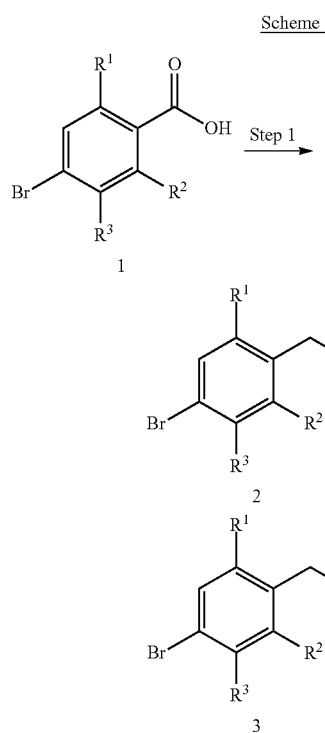

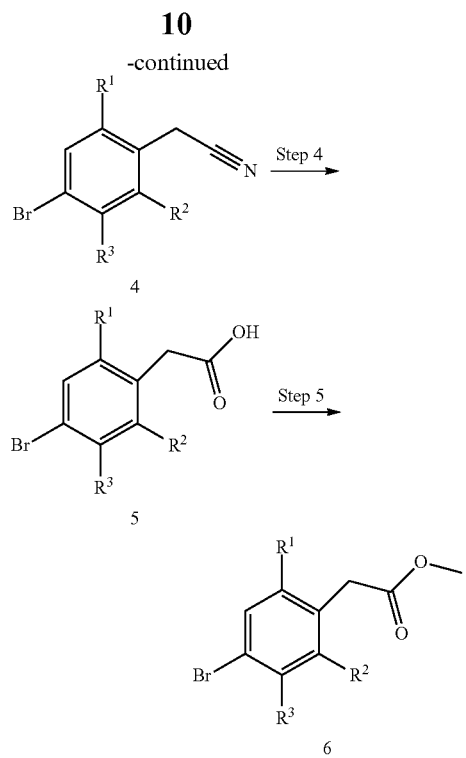

LG = leaving group
$R^1$, $R^2$, and $R^3$ are as defined for Formula I

Scheme 1 shows the synthesis of intermediate 6, which is used in the preparation of the compounds of Formula I. Benzoic acid 1 first undergoes reduction with borane dimethylsulfide complex in Step 1 to give alcohol 2. The alcohol is converted into a leaving group (LG, intermediate 3). For example, the alcohol in intermediate 2 can be converted to a mesylate group using methanesulfonyl chloride at −15° C. in Step 2, or it can be converted to a bromide using phosphorus tribromide at 0° C. Intermediate 3 is reacted with NaCN in Step 3 to give nitrile 4. Nitrile 4 is converted with KOH at elevated temperature in Step 4 to give acid 5, which is then esterified in Step 5 to give intermediate 6 using oxalyl chloride, DMF, and methanol.

Scheme 2

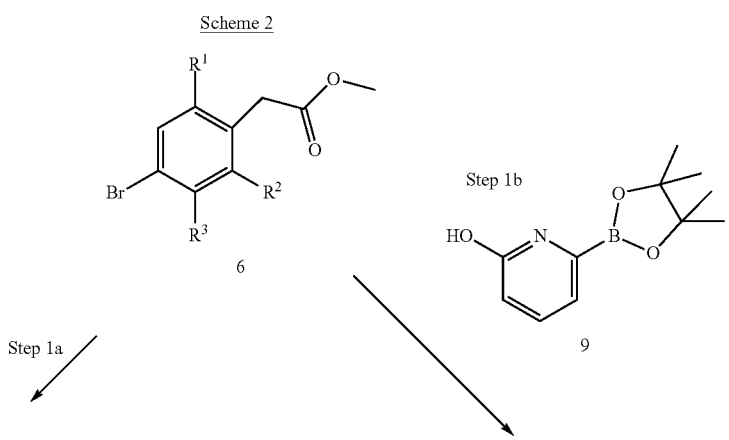

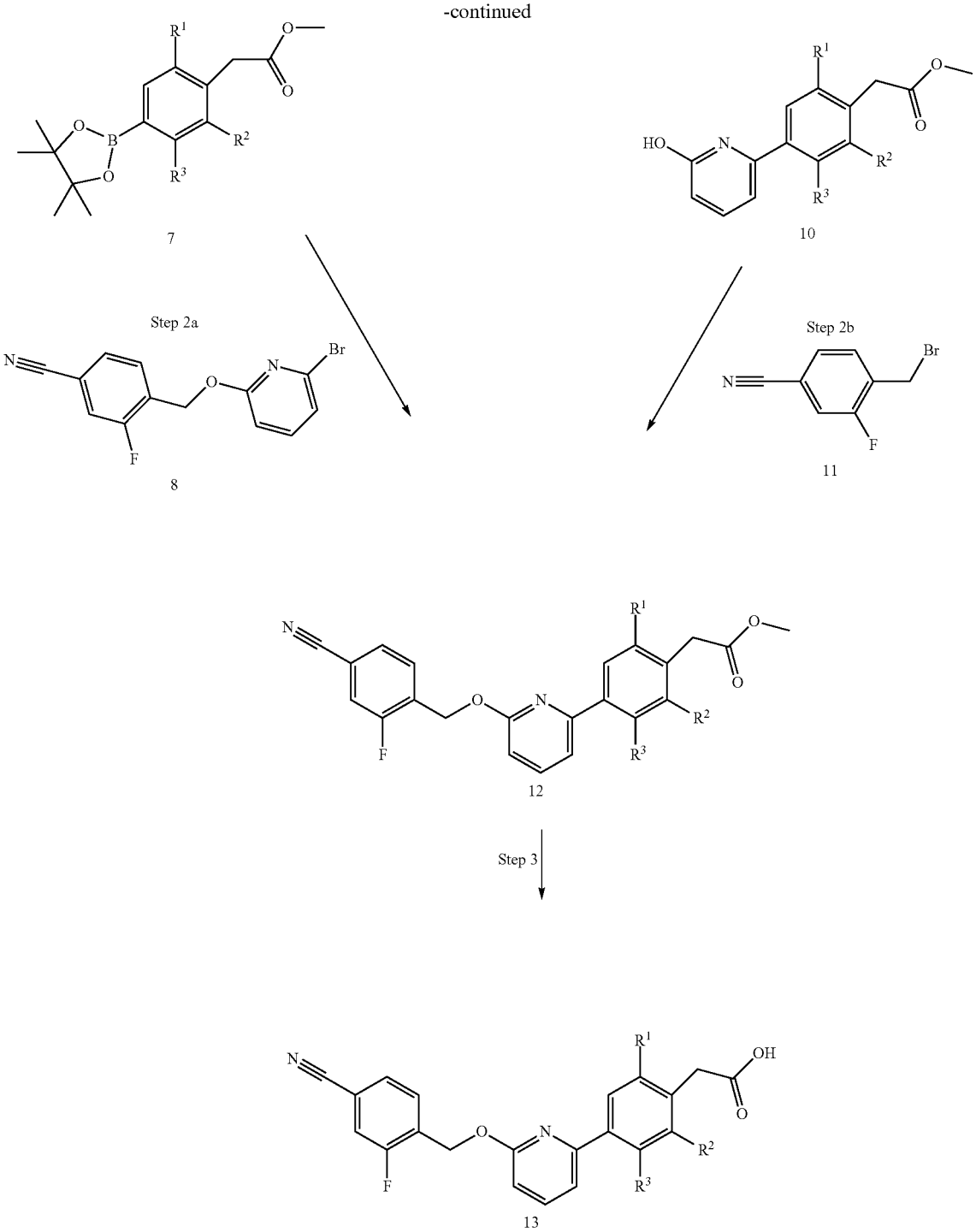

Scheme 2 depicts the preparation of key intermediate 12 for the preparation of the compounds of Formula I via two routes. In the first route, aryl halide 6 undergoes a one-pot Miyura borylation/Suzuki coupling: using bis(pinacolato)diboron, Pd(dppf)Cl$_2$, and potassium acetate at elevated temperature, aryl halide 6 is converted in Step 1a to boronic ester 7, whereupon bromopyridine 8 and K$_2$CO$_3$ are added to the reaction (Step 2a) giving intermediate 12. In the second route, a two-step process is employed: Suzuki coupling of aryl halide 6 with 6-hydroxypyridine-2-boronic acid pinacol ester 9 using Pd(dppf)Cl$_2$ and K$_2$CO$_3$ at elevated temperature (Step 1b) provides intermediate 10, which is then alkylated with 4-(bromomethyl)-3-fluorobenzonitrile 6 using Ag$_2$CO$_3$ at elevated temperature (Step 2b) to give intermediate 12. Ester hydrolysis of intermediate 12 in Step 3 using LiOH yields acid intermediate 13.

Scheme 3
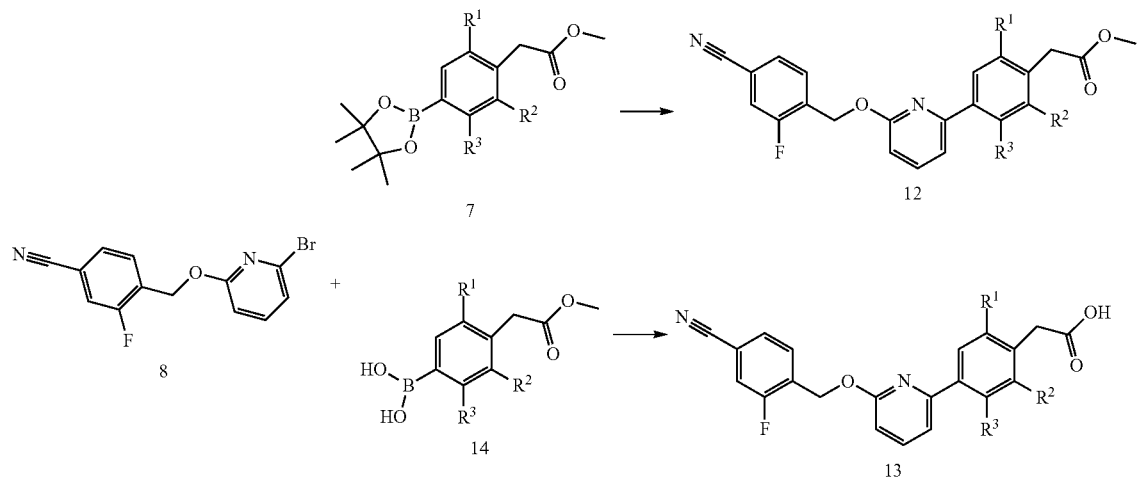
$R^1$, $R^2$, and $R^3$ are as defined for Formula I
Alternatively, key intermediates 12 and 13 can be prepared according to Scheme 3, coupling bromopyridine 8 with boronic ester 7 or boronic acid 14 using Pd(dppf)Cl$_2$ and potassium carbonate at elevated temperature.
Scheme 4
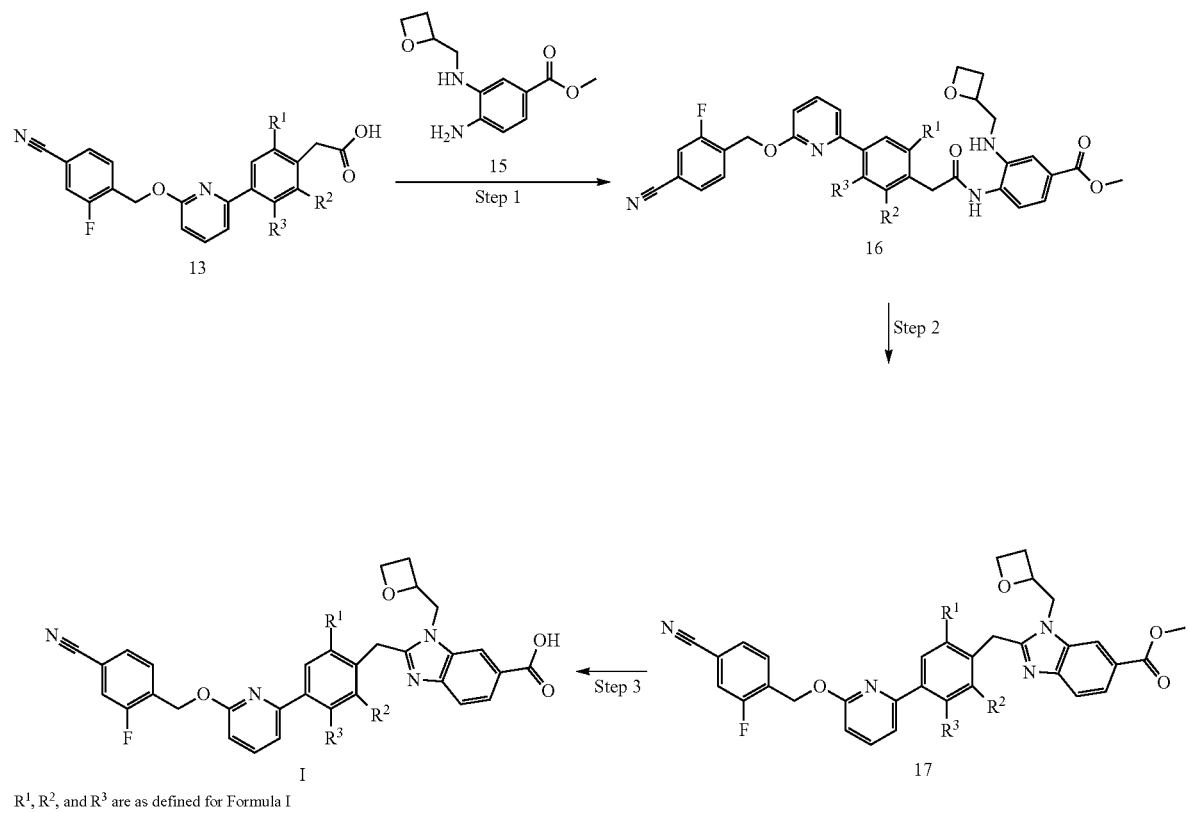
$R^1$, $R^2$, and $R^3$ are as defined for Formula I Scheme 4 shows the conversion of key intermediate 13 to compounds of Formula I. Amide coupling in Step 1 using HATU and dianiline 15 gives intermediate 16. Cyclization (Step 2) is accomplished by heating intermediate 16 in acetic acid to give benzimidazole 17. Finally, in Step 3 the compounds of Formula I are obtained by hydrolysis of 17 using LiOH.

PREPARATIONS AND EXAMPLES

LC-ES/MS is performed on an AGILENT©HP1200 liquid chromatography system. Electrospray mass spectrometry measurements (acquired in positive and/or negative mode) are performed on a Mass Selective Detector quadrupole mass spectrometer interfaced to an HPLC which may or may not have an ELSD. LC-ES/MS conditions (low pH): column: PHENOMENEX® GEMINI® NX C18 2.0×50 mm 3.0 μm, 110 Å; gradient: 5-95% B in 1.5 min, then 95% B for 0.5 min column temperature: 50° C.+/−10° C.; flow rate: 1.2 mL/min; 1 μL injection volume; Solvent A: deionized water with 0.1% HCOOH; Solvent B: ACN with 0.1% formic acid; wavelength 200-400 nm and 212-216 nm. If the HPLC is equipped with an ELSD the settings are 45° C. evaporator temperature, 40° C. nebulizer temperature, and 1.6 SLM gas flow rate. Alternate LC-MS conditions (high pH): column: Waters xBridge® C18 column 2.1×50 mm, 3.5 μm; gradient: 5-95% B in 1.5 min, then 95% B for 0.50 min; column temperature: 50° C.+/−10° C.; flow rate: 1.2 mL/min; 1 L injection volume; Solvent A: 10 mM $NH_4HCO_3$ pH 9; Solvent B: ACN; wavelength: 200-400 nm and 212-216 nm; if had ELSD: 45° C. evaporator temp, 40° C. nebulizer temp, and 1.60 SLM gas flow rate.

The X-ray powder diffraction (XRPD) patterns of crystalline solids are obtained on a Bruker D4 Endeavor X-ray powder diffractometer, equipped with a CuKα source and a Vantec detector, operating at 35 kV and 50 mA. The sample is scanned between 4 and 40 2θ°, with a step size of 0.008 2θ° and a scan rate of 0.5 seconds/step, and using 1.0 mm divergence, 6.6 mm fixed anti-scatter, and 11.3 mm detector slits. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

Preparation 1

(4-Bromo-2-fluoro-5-methylphenyl)methanol

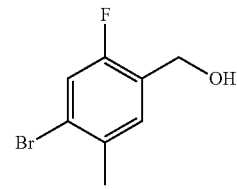

To a flask add: 4-bromo-2-fluoro-5-methylbenzoic acid (100 g, 421 mmol), THE (200 mL) and borane (dimethyl sulfide complex, 2 mol/L solution in THF, 210 mL, 10 mmol). Stir the mixture at RT overnight. Quench the reaction mixture with HCl (1.0 N aqueous solution, 50 mL) and filter the mixture. Concentrate the filtrate in-vacuo and partition the residue between EtOAc (400 mL) and water (400 mL). Wash the organics with saturated aqueous NaCl (400 mL), dry over $Na_2SO_4$, filter, and concentrate to give the title compound as solid (93.5 g, 99%). $^1$H-NMR (400 MHz, $CDCl_3$) δ 7.29 (d, J=7.9 Hz, 1H), 7.26 (d, J=9.1 Hz, 1H), 4.69 (s, 2H), 2.38 (s, 3H).

Preparation 2

(4-Bromo-2-fluoro-3-methyl-phenyl)methanol

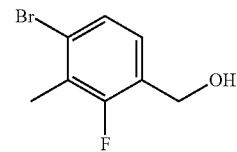

Prepare the title compound essentially as described in Preparation 1 using 4-bromo-2-fluoro-3-methylbenzoic acid. Purify the product by silica gel chromatography using a gradient of 10 to 35% EtOAc in hexanes. LC-ES/MS peak retention time: 1.01 min.

Preparation 3

2-(4-Bromo-2-fluoro-5-methylphenyl)acetonitrile

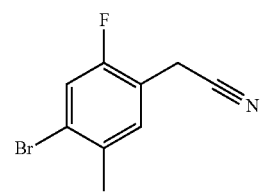

Dissolve (4-bromo-2-fluoro-5-methylphenyl)methanol (92 g, 420 mmol) in DCM (500 mL) and add triethylamine (120 mL, 861 mmol). Cool the mixture to −15° C. and add a solution of methanesulfonyl chloride (40 mL, 517 mmol) in DCM (30 mL) dropwise to the reaction mixture. Stir the mixture for 30 min at RT. Partition the reaction mixture between DCM (500 mL) and water (500 mL). Wash the organics with saturated aqueous NaCl (500 mL), dry over Na$_2$SO$_4$, filter, and concentrate. Dissolve the residue in DMF (400 mL) and cool the mixture with an ice bath. Add NaCN (21.0 g, 429 mmol) in one portion to the reaction mixture and stir at RT overnight. Partition the mixture between EtOAc (400 mL) and water (500 mL). Wash the organics with saturated aqueous NaCl (500 mL), dry over Na$_2$SO$_4$, filter, and concentrate. Purify the residue by silica gel chromatography using a gradient of 10 to 30% EtOAc in hexanes to give the title compound (47.0 g, 48%) as an oil. $^1$H-NMR (400 MHz, CDCl$_3$) δ 7.34 (d, J=8.7 Hz, 1H), 7.32 (d, J=8.1 Hz, 1H), 3.71 (s, 2H), 2.41 (s, 3H).

Preparation 4

2-(4-Bromo-2-fluoro-3-methyl-phenyl)acetonitrile

Mix together (4-bromo-2-fluoro-3-methyl-phenyl)methanol (1.90 g, 8.67 mmol) and DCM (20 mL). Cool the mixture to 0° C., then add phosphorus tribromide (1.0 mL, 11 mmol) dropwise. Stir the mixture at 0° C. for 15 min, then basify the mixture with saturated aqueous NaHCO$_3$ (10 mL). Extract the mixture with DCM (40 mL). Wash the organics with brine (30 mL), dry over (Na$_2$SO$_4$), filter and concentrate to give a solid. Dissolve the solid in DMSO (10 mL), then add NaCN (0.60 g, 13.0 mmol) and stir for 1 h. Partition the mixture between EtOAc (50 mL) and water (50 mL). Wash the organics with brine (50 mL), dry over Na$_2$SO$_4$, filter and concentrate to give the product as solid (1.3 g, 64%). LC-ES/MS peak retention time: 1.17 min Preparation 5

Methyl 2-(4-bromo-2-fluoro-5-methyl-phenyl)acetate

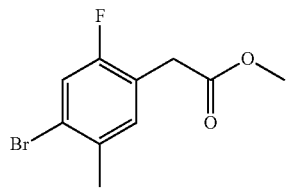

To a flask add: 2-(4-bromo-2-fluoro-5-methylphenyl)acetonitrile (1.20 g, 5.10 mmol), ethanol (5 mL), water (3 mL), and potassium hydroxide (0.90 g, 16 mmol). Heat the mixture at 90° C. overnight. Cool the mixture with an ice bath and acidify with 1.0 M HCl to pH 4-5, then partition the mixture between EtOAc (30 mL) and water (30 mL). Wash the organics with saturated aqueous NaCl (30 mL), dry over Na$_2$SO$_4$, filter, and concentrate to give 2-(4-bromo-2-fluoro-5-methyl-phenyl)acetic acid as solid. Dissolve this in DCM (10 mL), then add DMF (0.05 mL, 0.6 mmol) and oxalyl chloride (0.5 mL, 6 mmol) at RT. Stir the mixture RT for 30 min, then add MeOH (2 mL, 49.4 mmol) dropwise. After 30 min, remove the solvent in-vacuo and partition the residue between EtOAc (40 mL) and 5% NaHCO$_3$ (30 mL). Wash the organics with saturated aqueous NaCl (40 mL), dry over Na$_2$SO$_4$, filter, and concentrate to give the title compound as an oil (1.1 g, 80%). ES/MS m/z ($^{79}$Br,$^{81}$Br) 278,280 (M+NH$_4^+$).

Preparation 6

Methyl 2-(4-bromo-2-fluoro-3-methyl-phenyl)acetate

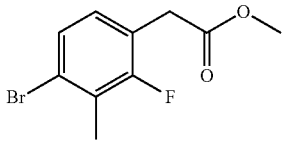

Prepare the title compound essentially as described in Preparation 5 using 2-(4-bromo-2-fluoro-3-methyl-phenyl)acetonitrile. LC-ES/MS peak retention time: 1.22 min.

Preparation 7

Methyl 2-(4-bromo-2,6-difluorophenyl)acetate

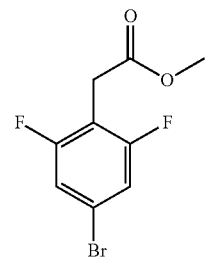

Mix 4-bromo-2,6-difluorophenylacetic acid (3.30 g, 12.5 mmol), DCM (20 mL), DMF (0.05 mL, 0.6 mmol), and oxalyl chloride (1.3 mL, 15 mmol). Stir the mixture at RT for 30 min. then add MeOH (1.5 mL, 37 mmol, 100 mass %) dropwise. Concentrate the mixture and partition between EtOAc (30 mL) and saturated aqueous NaHCO$_3$ (15 mL). Wash the organics with saturated aqueous NaCl (30 mL), dry over Na$_2$SO$_4$, filter, and concentrate to give the title compound as an oil (3.41 g, quantitative yield), which is used without further purification in Preparation 10. ES/MS m/z ($^{79}$Br,$^{81}$Br) 265,267 (M+H).

Preparation 8

4-[(6-Bromo-2-pyridyl)oxymethyl]-3-fluoro-benzonitrile

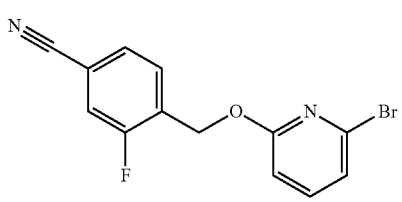 [SMILES: N#Cc1ccc(COc2cccc(Br)n2)c(F)c1]

Dissolve 2-bromo-6-fluoropyridine (2.50 g, 13.8 mmol) and 3-fluoro-4-(hydroxymethyl)benzonitrile (2.15 g, 13.8 mmol) in 1,4-dioxane (25 mL) and add a solution of potassium tert-butoxide (20 wt % in THF, 10.0 mL, 16.6 mmol) dropwise over 12 min at RT. Heat the reaction mixture at 40° C. for 30 min. Pour the mixture into aqueous $K_2CO_3$ (1M) and extract twice with EtOAc. Wash the organics with water and saturated aqueous NaCl, dry over $Na_2SO_4$, filter, and concentrate. Dry the residue in a vacuum oven at 50° C. to give the title compound (4.23 g, 95%) as a light yellow solid. ES/MS m/z ($^{79}$Br,$^{81}$Br) 307,309 (M+H).

Preparation 9

Methyl 2-[2-fluoro-4-(6-hydroxy-2-pyridyl)-5-methyl-phenyl]acetate

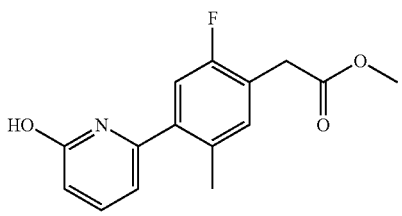 [SMILES: COC(=O)Cc1cc(C)c(-c2cccc(O)n2)cc1F]

To a flask add 6-hydroxypyridine-2-boronic acid pinacol ester (1.6 g, 6.9 mmol), methyl 2-(4-bromo-2-fluoro-5-methyl-phenyl)acetate (2.2 g, 8.4 mmol), THF (15 mL), water (1 mL), and potassium carbonate (2.0 g, 14 mmol). Purge the mixture with nitrogen for 10 min, then add Pd(dppf)Cl$_2$ (0.26 g, 0.35 mmol) and heat at 75° C. for 2 h. Partition the mixture between EtOAc (30 mL) and water (30 mL). Wash the organics with saturated aqueous NaCl (30 mL), dry over Na$_2$SO$_4$, filter and concentrate to give the title compound (1.4 g, 74%) as a solid. ES/MS m/z 276 (M+H), 274 (M−H).

Preparation 10

Methyl 2-[2,6-difluoro-4-(6-hydroxy-2-pyridyl)phenyl]acetate

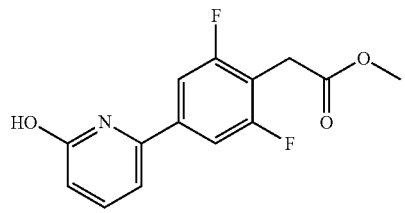 [SMILES: COC(=O)Cc1c(F)cc(-c2cccc(O)n2)cc1F]

Prepare the title compound essentially as described in Preparation 9 using methyl 2-(4-bromo-2,6-difluorophenyl)acetate, heating the reaction at 75° C. overnight. ES/MS m/z 280 (M+H).

Preparation 11

Methyl 2-[2-fluoro-4-(6-hydroxy-2-pyridyl)-3-methyl-phenyl]acetate

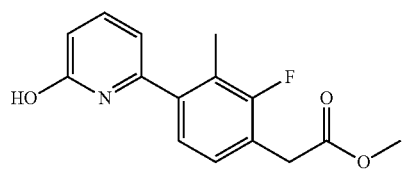 [SMILES: COC(=O)Cc1ccc(-c2cccc(O)n2)c(C)c1F]

Prepare the title compound essentially as described in Preparation 9 using methyl 2-(4-bromo-2-fluoro-3-methyl-phenyl)acetate, heating the reaction at 75° C. overnight (18 h). ES/MS m/z 276 (M+H), 274 (M−H).

Preparation 12

Methyl 2-[4-[6-[(4-cyano-2-fluoro-phenyl)methoxy]-2-pyridyl]-3-methyl-phenyl]acetate

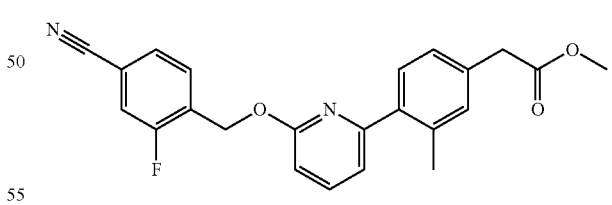

Dissolve 2-(4-bromo-3-methylphenyl)acetic acid (10.7 g, 45.8 mmol) in DCM (50 mL). Cool the mixture in an ice/water bath, and then add oxalyl chloride (4.8 mL, 55 mmol) and DMF (0.1 mL). Remove ice/water bath and stirred at RT for 2 h. Add MeOH (6.0 mL) dropwise over 2 min and stirred at RT for 1 h. Concentrate the reaction mixture in-vacuo and dissolve the residue in EtOAc. Wash the organics with saturated aqueous NaHCO$_3$ and saturated aqueous NaCl. Dry the organics over Na$_2$SO$_4$, then filter and concentrate. To the residue add bis(pinacolato)diboron (12.8 g, 50.4 mmol) and potassium acetate (13.6 g, 137 mmol).

Bubble nitrogen through the reaction mixture for 15 min, then add Pd(dppf)Cl₂ (complex with DCM, 1.13 g, 1.37 mmol). Heat the reaction under nitrogen at 85° C. for 15 h in an oil bath, then remove the reaction flask from the oil bath. Dissolve potassium carbonate (9.49 g, 68.7 mmol) in water (60 mL), bubble nitrogen through the solution for 10 min, and then add this solution to the reaction mixture followed by 4-[(6-bromo-2-pyridyl)oxymethyl]-3-fluoro-benzonitrile (14.1 g, 45.8 mmol). Bubble nitrogen through the entire reaction mixture for 5 min and heat under nitrogen at 85° C. for 6 h. Cool the reaction to near RT and concentrate in-vacuo to remove most of the 1,4-dioxane. Dilute this mixture with EtOAc (200 mL) and wash with water and saturated aqueous NaCl. Dry the organics over Na₂SO₄, then filter and concentrate. Purify the crude product by silica gel chromatography using a gradient of 5 to 50% EtOAc in hexanes to give the title compound (13.3 g, 70%) as a light yellow solid. ES/MS m/z 391 (M+H).

Preparation 13

Methyl 2-[4-[6-[(4-cyano-2-fluoro-phenyl)methoxy]-2-pyridyl]-2-fluoro-5-methyl-phenyl]acetate

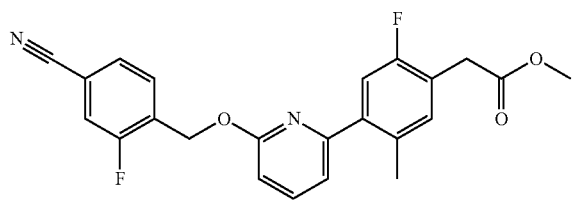 [SMILES: COC(=O)Cc1cc(C)c(-c2cccc(OCc3ccc(C#N)cc3F)n2)cc1F]

To a flask add methyl 2-[2-fluoro-4-(6-hydroxy-2-pyridyl)-5-methyl-phenyl]acetate (1.40 g, 5.09 mmol), 1,4-dioxane (35 mL), silver carbonate (1.7 g, 6.2 mmol), and 4-(bromomethyl)-3-fluorobenzonitrile (1.4 g, 6.2 mmol). Heat the mixture at 60° C. overnight. Filter off the solid and concentrate the filtrate. Purified the residue by silica gel chromatography using 12 to 55% EtOAc in hexanes to give the title compound (1.60 g, 77% as a solid. ES/MS m/z 409 (M+H), 407 (M–H).

Preparation 14

Methyl 2-[4-[6-[(4-cyano-2-fluoro-phenyl)methoxy]-2-pyridyl]-2-fluoro-phenyl]acetate

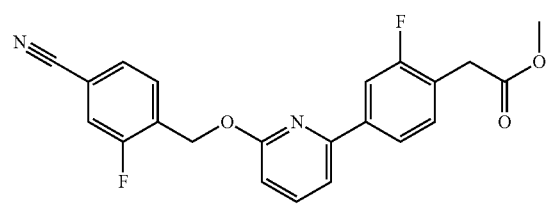 [SMILES: COC(=O)Cc1ccc(-c2cccc(OCc3ccc(C#N)cc3F)n2)cc1F]

Charge a flask with 4-[(6-bromo-2-pyridyl)oxymethyl]-3-fluoro-benzonitrile (2.02 g, 6.58 mmol), methyl 2-(2-fluoro-4-(4,4,5,5-tetramethyl-1,3,2-dioxaborolan-2-yl)phenyl)acetate (2.99 g, 9.88 mmol), K₂CO₃ (2.30 g, 16.5 mmol), 1,4-dioxane (30 mL) and water (10 mL). Bubble nitrogen through the mixture for 10 min. Add Pd(dppf)Cl₂ DCM complex (492 mg, 0.658 mmol) to the mixture and heat to 80° C. under nitrogen for 5 h. Cool the reaction mixture, dilute with EtOAc (75 mL) and filter through a pad of Celite®. Wash the filtrate with water and saturated aqueous NaCl, dried over Na₂SO₄, filtered and concentrated. Purify the resulting residue by silica gel chromatography with a gradient of 5 to 90% EtOAc in hexanes to obtain the title compound (2.68 g, 94%). ES/MS m/z 395 (M+H).

Preparation 15

Methyl 2-[4-[6-[(4-cyano-2-fluoro-phenyl)methoxy]-2-pyridyl]-2,6-difluoro-phenyl]acetate

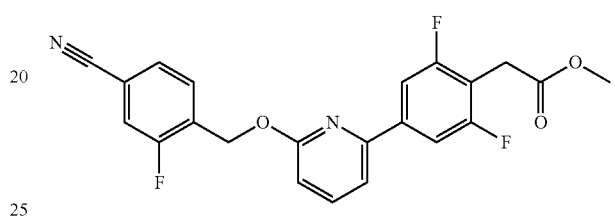

Prepare the title compound essentially as described in Preparation 13 using methyl 2-[2,6-difluoro-4-(6-hydroxy-2-pyridyl)phenyl]acetate, heating the reaction at 80° C. overnight. ES/MS m/z 413 (M+H).

Preparation 16

Methyl 2-[4-[6-[(4-cyano-2-fluoro-phenyl)methoxy]-2-pyridyl]-2-fluoro-3-methyl-phenyl]acetate

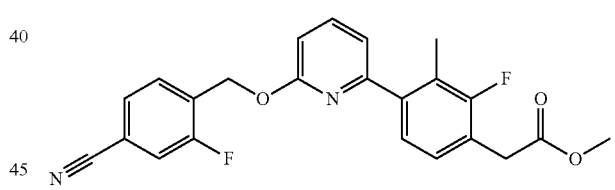

Prepare the title compound essentially as described in Preparation 13 using methyl 2-[2-fluoro-4-(6-hydroxy-2-pyridyl)-3-methyl-phenyl]acetate, heating the reaction at 80° C. for 3 h. ES/MS m/z 409 (M+H).

Preparation 17

2-[4-[6-[(4-Cyano-2-fluoro-phenyl)methoxy]-2-pyridyl]-3-methyl-phenyl]acetic Acid

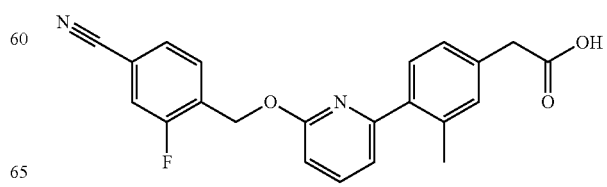

To a flask add methyl 2-[4-[6-[(4-cyano-2-fluoro-phenyl)methoxy]-2-pyridyl]-3-methyl-phenyl]acetate (1.20 g, 3.07 mmol), ACN (20 mL), water (10 mL), and lithium hydroxide (0.35 g, 15 mmol). Heat the mixture at 45° C. for 3 h. Cool the mixture with an ice bath and acidify with 1.0 M HCl to pH=4-5. Partition the mixture between EtOAc (30 mL) and water (30 mL). Wash the organics with brine (30 mL), dry over Na₂SO₄, filter, and concentrate to give the title compound (1.1 g, 95%) as solid. ES/MS m/z 377 (M+H).

Preparation 18

2-[4-[6-[(4-Cyano-2-fluoro-phenyl)methoxy]-2-pyridyl]-2-fluoro-5-methyl-phenyl]acetic Acid

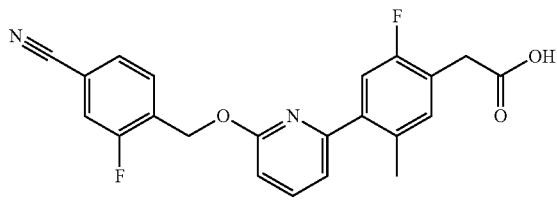 [SMILES: Cc1cc(CC(=O)O)c(F)cc1-c1cccc(OCc2ccc(C#N)cc2F)n1]

To a vial add methyl 2-[4-[6-[(4-cyano-2-fluoro-phenyl)methoxy]-2-pyridyl]-2-fluoro-5-methyl-phenyl]acetate (1.6 g, 3.9 mmol), ACN (20 mL), water (6 mL), and lithium hydroxide (0.45 g, 19 mmol). Heat the mixture at 45° C. for 2 h, cool the mixture with an ice bath, and acidify with 1.0 M HCl to pH=4-5. Partition the mixture between EtOAc (50 mL) and water (50 mL). Wash the organics with saturated aqueous NaCl (50 mL), dry over Na₂SO₄, filter and concentrated to give the title compound (1.55 g, 100%) as solid. ES/MS m/z 395 (M+H).

Preparation 19

2-[4-[6-[(4-Cyano-2-fluoro-phenyl)methoxy]-2-pyridyl]-2-fluoro-phenyl]acetic Acid

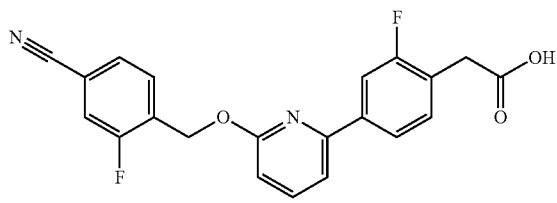 [SMILES: N#Cc1ccc(COc2cccc(-c3ccc(CC(=O)O)c(F)c3)n2)c(F)c1]

Dissolve methyl 2-[4-[6-[(4-cyano-2-fluoro-phenyl)methoxy]-2-pyridyl]-2-fluoro-phenyl]acetate (2.68 g, 6.25 mmol) in THF (50 mL), then add lithium hydroxide (797 mg, 32.9 mmol) and water (20 mL). After stirring at RT for 5 h, adjust the pH of the reaction mixture to 5 with aqueous HCl (1M). Remove volatile solvents in-vacuo to give an aqueous slurry. Filter and dry the solid to obtain the title compound (2.24 g, 88%). ES/MS m/z 381 (M+H).

Preparation 20

2-[4-[6-[(4-Cyano-2-fluoro-phenyl)methoxy]-2-pyridyl]-2,6-difluoro-phenyl]acetic Acid

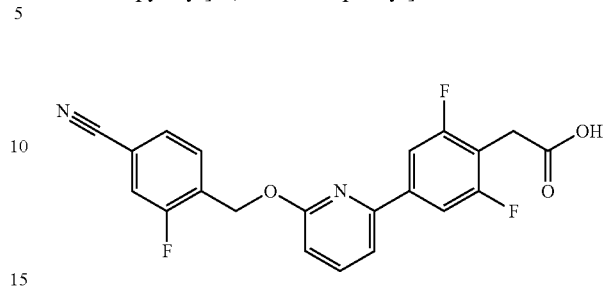

Prepare the title compound essentially as described in Preparation 18 using methyl 2-[4-[6-[(4-cyano-2-fluoro-phenyl)methoxy]-2-pyridyl]-2,6-difluoro-phenyl]acetate. ES/MS m/z 399 (M+H).

Preparation 21

2-[4-[6-[(4-Cyano-2-fluoro-phenyl)methoxy]-2-pyridyl]-2-fluoro-3-methyl-phenyl]acetic Acid

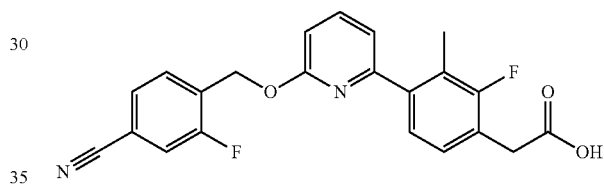

Prepare the title compound essentially as described in Preparation 17 using methyl 2-[4-[6-[(4-cyano-2-fluoro-phenyl)methoxy]-2-pyridyl]-2-fluoro-3-methyl-phenyl]acetate. ES/MS m/z 395 (M+H).

Preparation 22

2-[4-[6-[(4-Cyano-2-fluoro-phenyl)methoxy]-2-pyridyl]phenyl]acetic Acid

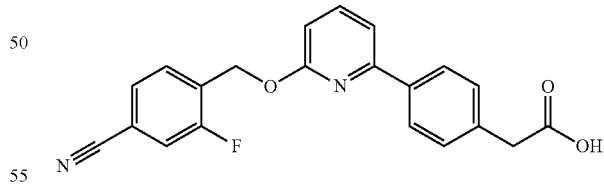

Mix together 4-[(6-bromo-2-pyridyl)oxymethyl]-3-fluoro-benzonitrile (0.70 g, 2.3 mmol) and 2-(4-boronophenyl)acetic acid (0.64 g, 3.4 mmol), THF (15 mL), water (5 mL) and potassium carbonate (0.63 g, 4.6 mmol). Purge the mixture with nitrogen for 10 min, then add Pd(dppf)Cl₂ (0.085 g, 0.11 mmol) and heat the mixture at 75° C. for 8 h. Acidify the mixture to pH 4-5 with aqueous HCl (1 M). Partition the mixture between EtOAc (50 mL) and water (50 mL). Wash the organics with brine (50 mL), dry over (Na₂SO₄), then filter and concentrate. Purify the residue by silica gel chromatography using a gradient of 25 to 65%

EtOAc in hexanes to give the title compound (800 mg, 97% yield) as solid. ES/MS m/z 363.0 (M+H).

Preparation 23

Methyl 4-amino-3-[[(2S)-oxetan-2-ylmethyl]amino]benzoate

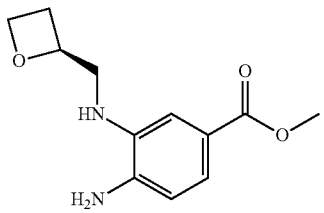 [SMILES: COC(=O)c1ccc(N)c(NC[C@@H]2CCO2)c1]

To a solution of methyl 3-fluoro-4-nitro-benzoate (2.0 g, 10 mmol) in THF (10 mL) and DMF (10 mL) add triethylamine (3.1 mL, 22 mmol) at RT. To the slightly yellow solution add [(2S)-oxetan-2-yl]methanamine (Austin Chemical Company, 1.0 g, 11 mmol) and stir the rust-colored solution overnight. Dilute the reaction with EtOAc (100 mL) and water (50 mL). Separate the organic layer and then back-extract the aqueous layer with EtOAc (2×50 mL). Combine the organics and wash with saturated aqueous NaCl. Dry the organics over $Na_2SO_4$, filter, concentrate, and dry the residue under high vacuum. This gives crude methyl 4-nitro-3-[[(2S)-oxetan-2-ylmethyl]amino]benzoate (2.8 g, 10 mmol) as a yellow solid (ES/MS m/z 267 (M+H)).

Next, dissolve methyl 4-nitro-3-[[(2S)-oxetan-2-ylmethyl]amino]benzoate (2.8 g, 10 mmol) in THF (50 mL) and add palladium on carbon (5% pre-wetted with water, 0.5 g). Vacuum purge the reaction mixture with hydrogen then stir under a balloon of hydrogen at RT for 2 h, during which time the yellow color vanishes. Filter the mixture through Celite© and concentrate to give the title compound (2.4 g, 99%). ES/MS m/z 237 (M+H).

Preparation 24

Methyl 4-[[2-[4-[6-[(4-cyano-2-fluoro-phenyl)methoxy]-2-pyridyl]-3-methyl-phenyl]acetyl]amino]-3-[[(2S)-oxetan-2-ylmethyl]amino]benzoate

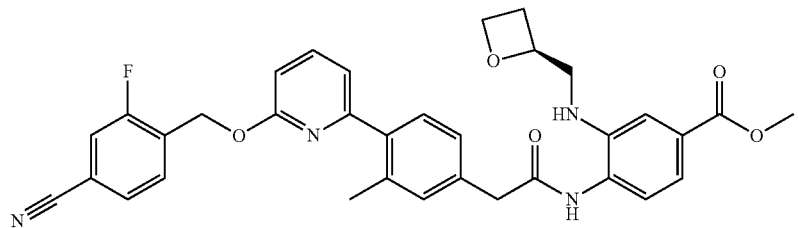 [SMILES: COC(=O)c1ccc(NC(=O)Cc2ccc(-c3cccc(OCc4ccc(C#N)cc4F)n3)c(C)c2)c(NC[C@@H]2CCO2)c1]

To a vial add 2-[4-[6-[(4-cyano-2-fluoro-phenyl)methoxy]-2-pyridyl]-3-methyl-phenyl]acetic acid (1.10 g, 2.92 mmol), DMF (10 mL), HATU (1.4 g, 3.6 mmol), methyl 4-amino-3-[[(2S)-oxetan-2-ylmethyl]amino]benzoate (0.76 g, 3.2 mmol), and DIPEA (1.5 mL, 8.6 mmol). Stir the mixture at RT for 30 min, then partition between EtOAc (30 mL) and water (30 mL). Wash the organics with saturated aqueous NaCl (30 mL), then dry over $Na_2SO_4$, filter, and concentrate. Purify the residue by silica gel chromatography using a gradient of 10 to 35% EtOAc in DCM to give the title compound (1.2 g, 69%) as solid. ES/MS m/z 595 (M+1), 593 (M−1).

Preparation 25

Methyl 4-[[2-[4-[6-[(4-cyano-2-fluoro-phenyl)methoxy]-2-pyridyl]-2-fluoro-5-methyl-phenyl]acetyl]amino]-3-[[(2S)-oxetan-2-ylmethyl]amino]benzoate

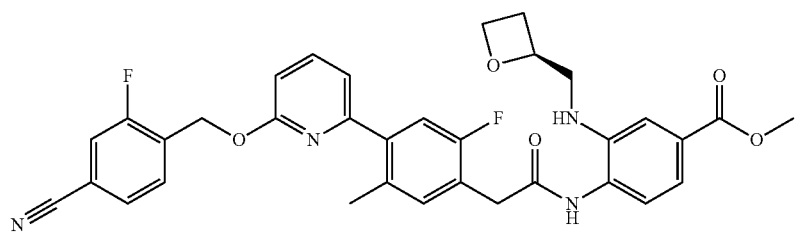 [SMILES: COC(=O)c1ccc(NC(=O)Cc2cc(C)c(-c3cccc(OCc4ccc(C#N)cc4F)n3)cc2F)c(NC[C@@H]2CCO2)c1]

To a flask add: 2-[4-[6-[(4-cyano-2-fluoro-phenyl)methoxy]-2-pyridyl]-2-fluoro-5-methyl-phenyl]acetic acid (1.20 g, 3.04 mmol), DMF (15 mL), HATU (1.2 g, 3.1 mmol), methyl 4-amino-3-[[(2S)-oxetan-2-ylmethyl]amino]benzoate (0.80 g, 3.4 mmol) and DIPEA (1.5 mL, 8.6 mmol). Stir the mixture at RT for 30 min, then partition between EtOAc (30 mL) and water (30 mL). Wash the organics with saturated aqueous NaCl (30 mL), then dry over Na$_2$SO$_4$, filter and concentrate. Purify the residue by silica gel chromatography using a gradient of 10 to 35% EtOAc in DCM to give the title compound as solid (1.20 g, 64%). ES/MS m/z 613 (M+1), 611 (M−H).

Preparation 26

Methyl 2-[[4-[6-[(4-cyano-2-fluoro-phenyl)methoxy]-2-pyridyl]-2-fluoro-phenyl]methyl]-3-[[(2S)-oxetan-2-yl]methyl]benzimidazole-5-carboxylate

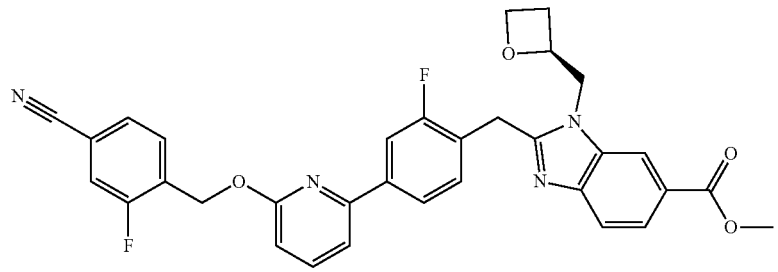 [SMILES: COC(=O)c1ccc2nc(Cc3ccc(-c4cccc(OCc5ccc(C#N)cc5F)n4)cc3F)n(C[C@@H]3CCO3)c2c1]

To a round-bottom flask add 2-[4-[6-[(4-cyano-2-fluoro-phenyl)methoxy]-2-pyridyl]-2-fluoro-phenyl]acetic acid (205 mg, 0.540 mmol), methyl 4-amino-3-[[(2S)-oxetan-2-ylmethyl]amino]benzoate (116 mg, 0.490 mmol), HATU (224 mg, 0.589 mmol), DIPEA (0.26 mL, 1.5 mmol), and DMF (5 mL). After stirring at RT for 3.5 h, dilute the reaction mixture with EtOAc (30 mL) and wash with water and saturated aqueous NaCl. Dry the organics over Na$_2$SO$_4$, filter, and concentrate. Purify the residue by silica gel chromatography using a gradient of 0 to 10% MeOH in DCM to obtain the intermediate amide (326 mg). ES/MS m/z 599 (M+H).

Heat the intermediate amide with acetic acid (5 mL) at 50° C. for 15 h. Concentrate the reaction mixture in-vacuo and dissolve the remaining residue in EtOAc (25 mL). Wash the organics with saturated aqueous NaHCO$_3$ and saturated aqueous NaCl. Dry the organics over Na$_2$SO$_4$, filtered and concentrate. Purify the resulting by silica gel chromatography using a gradient of 20 to 100% EtOAc in hexanes to obtain the title compound (152 mg, 52%). ES/MS m/z 581 (M+H).

Preparation 27

Methyl 4-[[2-[4-[6-[(4-cyano-2-fluoro-phenyl)methoxy]-2-pyridyl]-2,6-difluoro-phenyl]acetyl]amino]-3-[[(2S)-oxetan-2-ylmethyl]amino]benzoate

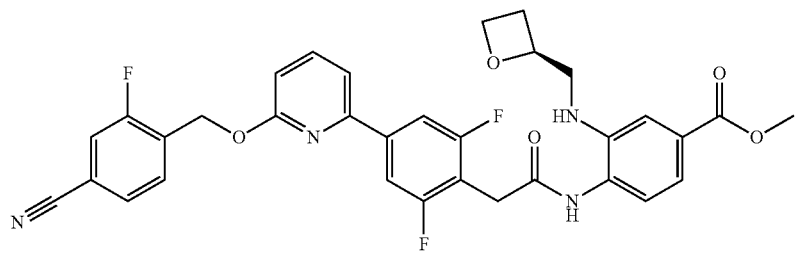 [SMILES: COC(=O)c1ccc(NC(=O)Cc2c(F)cc(-c3cccc(OCc4ccc(C#N)cc4F)n3)cc2F)c(NC[C@@H]2CCO2)c1]

Prepare the title compound essentially as described in Preparation 24 using 2-[4-[6-[(4-cyano-2-fluoro-phenyl)methoxy]-2-pyridyl]-2,6-difluoro-phenyl]acetic acid. Collect the product which precipitates during the aqueous workup by filtration and use without further purification. ES/MS m/z 617 (M+H), 615 (M−H).

Preparation 28

Methyl 4-[[2-[4-[6-[(4-cyano-2-fluoro-phenyl)methoxy]-2-pyridyl]-2-fluoro-3-methyl-phenyl]acetyl]amino]-3-[[(2S)-oxetan-2-ylmethyl]amino]benzoate

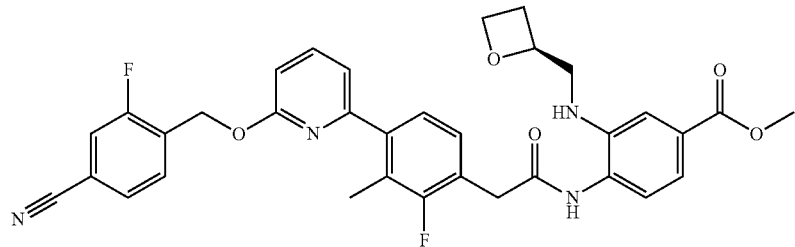 [SMILES: COC(=O)c1ccc(NC(=O)Cc2ccc(-c3cccc(OCc4ccc(C#N)cc4F)n3)c(C)c2F)c(NC[C@@H]2CCO2)c1]

Prepare the title compound essentially as described in Preparation 24 using 2-[4-[6-[(4-cyano-2-fluoro-phenyl)methoxy]-2-pyridyl]-2-fluoro-3-methyl-phenyl]acetic acid. ES/MS m/z 613 (M+H), 611 (M−H).

Preparation 29

Methyl 4-[[2-[4-[6-[(4-cyano-2-fluoro-phenyl)methoxy]-2-pyridyl]phenyl]acetyl]amino]-3-[[(2S)-oxetan-2-ylmethyl]amino]benzoate

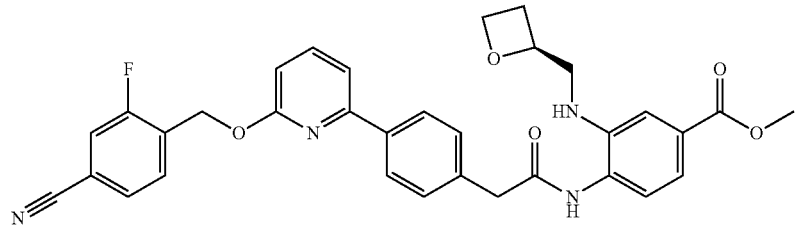 [SMILES: COC(=O)c1ccc(NC(=O)Cc2ccc(-c3cccc(OCc4ccc(C#N)cc4F)n3)cc2)c(NC[C@@H]2CCO2)c1]

Prepare the title compound essentially as described in Preparation 25 using 2-[4-[6-[(4-cyano-2-fluoro-phenyl)methoxy]-2-pyridyl]phenyl]acetic acid. ES/MS m/z 581.0 (M+H), 579.0 (M−H).

Example 1

2-[[4-[6-[(4-Cyano-2-fluoro-phenyl)methoxy]-2-pyridyl]-3-methyl-phenyl]methyl]-3-[[(2S)-oxetan-2-yl]methyl]benzimidazole-5-carboxylic Acid

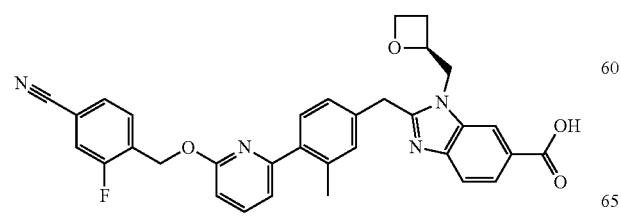

To a vial add methyl 4-[[2-[4-[6-[(4-cyano-2-fluoro-phenyl)methoxy]-2-pyridyl]-3-methyl-phenyl]acetyl]amino]-3-[[(2S)-oxetan-2-ylmethyl]amino]benzoate (1.2 g, 2.0 mmol) and acetic acid (6 mL). Heat the mixture at 80° C. for 2 h, then remove the solvent in-vacuo. Partition the residue between EtOAc (30 mL) and aqueous NaHCO$_3$ (5%, 20 mL). Wash the organics with saturated aqueous NaCl (30 mL), dry over Na$_2$SO$_4$, filter, and concentrate. Dissolve the residue in ACN (5 mL) and water (3 mL), then add to the mixture LiOH (0.22 g, 9.2 mmol) and stir at 50° C. for 2 h. Remove the solvent in-vacuo. Purify the residue by reverse-phase flash chromatography using a gradient of 20 to 35% ACN in 5% aqueous NH$_4$HCO$_3$ to give the title compound (900 mg, 79%) as a solid. ES/MS m/z 563 (M+H), 561 (M−H).

To a vial add methyl 4-[[2-[4-[6-[(4-cyano-2-fluoro-phenyl)methoxy]-2-pyridyl]-2-fluoro-5-methyl-phenyl]acetyl]amino]-3-[[(2S)-oxetan-2-ylmethyl]amino]benzoate (1.20 g, 1.96 mmol) and acetic acid (15 mL), then heat the mixture at 80° C. for 2 h. Remove the solvent in-vacuo. Partition the residue between EtOAc (30 mL) and aqueous NaHCO$_3$ (5%, 20 mL). Wash the organics with saturated aqueous NaCl (30 mL), dry over Na$_2$SO$_4$, filter, and concentrate. Dissolve the residue in ACN (10 mL) and water (4 mL), then add to the mixture LiOH (0.24 g, 10 mmol) and stir at 50° C. for 2 h. Acidify the mixture with saturated aqueous citric acid to pH=4-5. Remove the solvent in-vacuo. Purify the residue by reverse-phase flash chromatography using a gradient of 20 to 35% ACN in 5% aqueous NH$_4$HCO$_3$ to give the title compound (745 mg, 66%) as a solid. ES/MS m/z 581 (M+H), 579 (M−H).

Example 2

2-[[4-[6-[(4-Cyano-2-fluoro-phenyl)methoxy]-2-pyridyl]-2-fluoro-5-methyl-phenyl]methyl]-3-[[(2S)-oxetan-2-yl]methyl]benzimidazole-5-carboxylic Acid

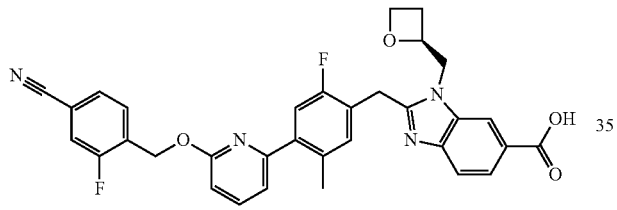

Example 2a tert-Butylammonium; 2-[[4-[6-[(4-cyano-2-fluoro-phenyl)methoxy]-2-pyridyl]-2-fluoro-5-methyl-phenyl]methyl]-3-[[(2S)-oxetan-2-yl]methyl]benzimidazole-5-carboxylate

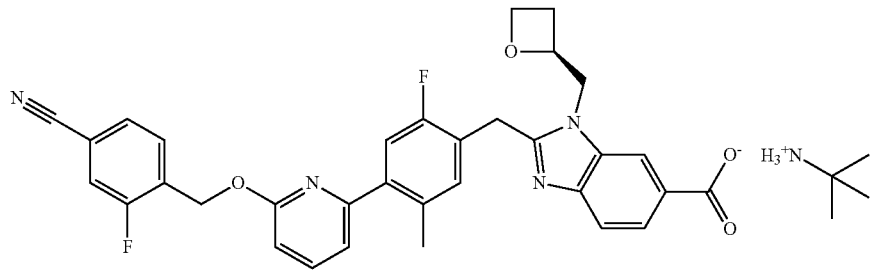

Method 1—Preparation without Seed Crystals

Suspend 2-[[4-[6-[(4-cyano-2-fluoro-phenyl)methoxy]-2-pyridyl]-2-fluoro-5-methyl-phenyl]methyl]-3-[[(2S)-oxetan-2-yl]methyl]benzimidazole-5-carboxylic acid (555 mg, 0.96 mmol) in acetone (6 mL) while stirring at 800 rpm at 50° C., giving a slurry of white solid. Add tert-butylamine (115 µL, 1.09 mmol, 1.14 eq) observing a brief clarification of the mixture followed by precipitation of a white solid. Stir this slurry at 50° C. for 1 h, then turn off heating and allow the sample to stir as it comes to RT. Filter off the solid by vacuum filtration and dry in place for 15 min under a stream of nitrogen, then dry in-vacuo at 50° C. for 1 h to give the title compound (612 mg, 98%).

Method 2—Preparation with Seed Crystals

Mix together 2-[[4-[6-[(4-cyano-2-fluoro-phenyl)methoxy]-2-pyridyl]-2-fluoro-5-methyl-phenyl]methyl]-3-[[(2S)-oxetan-2-yl]methyl]benzimidazole-5-carboxylic acid (50 g, 86.1 mmol), acetone (658 mL), and water (42 mL), and heat the mixture 50° C. Filter the mixture over GF/F paper and rinse with 94:6 v:v acetone:water (25 mL). Heat the resulting solution at 50° C. Prepare a solution of tert-butylamine (10 mL, 94.7 mmol, 1.1 eq) and 94:6 v:v acetone:water (25 mL). Add a portion of the tert-butylamine solution (7 mL) followed by seed crystals of tert-butylammonium; 2-[[4-[6-[(4-cyano-2-fluoro-phenyl)methoxy]-2-pyridyl]-2-fluoro-5-methyl-phenyl]methyl]-3-[[(2S)-oxetan-2-yl]methyl]benzimidazole-5-carboxylate (50 mg). Add the remaining tert-butylamine solution over approximately 1 h via syringe pump at a rate of 0.47 mL/min. Heat the resulting suspension at 50° C. for 2 h, then cool the mixture to ambient temperature overnight. Filter the slurry and rinse with acetone (2×100 mL). Dry the wetcake at 50° C. in-vacuo to a constant weight to give the title compound (51.8 g, 92%) as a pale yellow solid.

A prepared sample of the title compound is characterized by an XRD pattern using CuKα radiation as having diffraction peaks (2-theta values) as described in Table 1 below, and in particular having peaks at 6.9 in combination with one or more of the peaks selected from the group consisting of 16.3 and 22.5; with a tolerance for the diffraction angles of 0.2 degrees.

TABLE 1

X-ray powder diffraction peaks of tert-butylammonium; 2-[[4-[6-[(4-cyano-2-fluoro-phenyl)methoxyl-2-pyridyl]-2-fluoro-5-methyl-phenyl]methyl]-3-[[(2S)-oxetan-2-yl]methyl]benzimidazole-5-carboxylate

| Peak | Angle (°2-Theta) +/−0.2° | Relative Intensity (% of most intense peak) |
|---|---|---|
| 1 | 5.5 | 26.20% |
| 2 | 6.9 | 64.90% |
| 3 | 11.2 | 49.20% |
| 4 | 16.3 | 100.00% |
| 5 | 17.1 | 34.70% |
| 6 | 19.6 | 53.00% |
| 7 | 21.8 | 43.10% |
| 8 | 22.5 | 93.80% |
| 9 | 27.3 | 41.10% |
| 10 | 28.0 | 37.90% |

Example 3

2-[[4-[6-[(4-Cyano-2-fluoro-phenyl)methoxy]-2-pyridyl]-2-fluoro-phenyl]methyl]-3-[(2S)-oxetan-2-ylmethyl]benzimidazole-5-carboxylic Acid

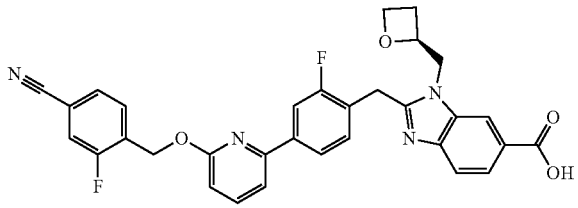 [SMILES: N#Cc1ccc(COc2cccc(-c3ccc(Cc4nc5ccc(C(=O)O)cc5n4C[C@@H]4CCO4)c(F)c3)n2)c(F)c1]

Dissolve methyl 2-[[4-[6-[(4-cyano-2-fluoro-phenyl)methoxy]-2-pyridyl]-2-fluoro-phenyl]methyl]-3-[[(2S)-oxetan-2-yl]methyl]benzimidazole-5-carboxylate (152 mg, 0.256 mmol) in THF (6 mL), then add lithium hydroxide (31 mg, 1.26 mmol) and water (2 mL). Stir the mixture at RT for 16 h, then adjust the pH to 6 with aqueous HCl (1N). Remove the THF in-vacuo and collect the remaining solid by filtration. Purify by reverse-phase flash chromatography using a gradient of 10 to 40% ACN in aqueous $NH_4HCO_3$ (10 mM, pH 10) to obtain the title compound (60 mg, 41%). ES/MS m/z 567 (M+H).

Example 4

2-[[4-[6-[(4-Cyano-2-fluoro-phenyl)methoxy]-2-pyridyl]-2,6-difluoro-phenyl]methyl]-3-[(2S)-oxetan-2-ylmethyl]benzimidazole-5-carboxylic Acid

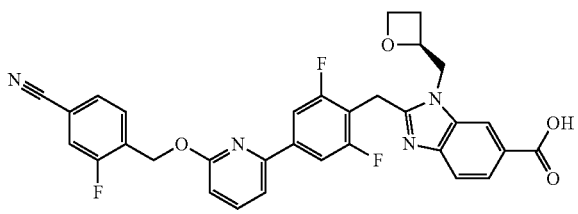 [SMILES: N#Cc1ccc(COc2cccc(-c3cc(F)c(Cc4nc5ccc(C(=O)O)cc5n4C[C@@H]4CCO4)c(F)c3)n2)c(F)c1]

Prepare the title compound essentially as described in Example 1 using methyl 4-[[2-[4-[6-[(4-cyano-2-fluoro-phenyl)methoxy]-2-pyridyl]-2,6-difluoro-phenyl]acetyl]amino]-3-[[(2S)-oxetan-2-ylmethyl]amino]benzoate. Purify the product by reverse-phase flash chromatography using a gradient of 30 to 50% ACN in aqueous $NH_4HCO_3$ (10 mM, pH 10). ES/MS m/z 585 (M+H), 583 (M−H).

Example 5

2-[[4-[6-[(4-Cyano-2-fluoro-phenyl)methoxy]-2-pyridyl]-2-fluoro-3-methyl-phenyl]methyl]-3-[[(2S)-oxetan-2-yl]methyl]benzimidazole-5-carboxylic Acid

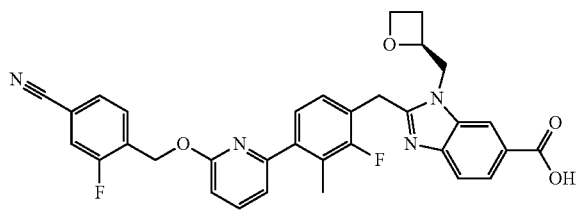 [SMILES: Cc1c(-c2cccc(OCc3ccc(C#N)cc3F)n2)ccc(Cc2nc3ccc(C(=O)O)cc3n2C[C@@H]2CCO2)c1F]

Prepare the title compound essentially as described in Example 2 using methyl 4-[[2-[4-[6-[(4-cyano-2-fluoro-phenyl)methoxy]-2-pyridyl]-2-fluoro-3-methyl-phenyl]acetyl]amino]-3-[[(2S)-oxetan-2-ylmethyl]amino]benzoate. Purify the product by reverse-phase flash chromatography using a gradient of 5 to 40% ACN in 5% aqueous $NH_4HCO_3$. ES/MS m/z 581 (M+H), 579 (M−H).

Example 6

2-[[4-[6-[(4-Cyano-2-fluoro-phenyl)methoxy]-2-pyridyl]phenyl]methyl]-3-[[(2S)-oxetan-2-yl]methyl]benzimidazole-5-carboxylic Acid

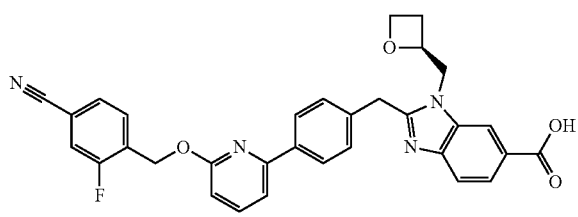 [SMILES: N#Cc1ccc(COc2cccc(-c3ccc(Cc4nc5ccc(C(=O)O)cc5n4C[C@@H]4CCO4)cc3)n2)c(F)c1]

Prepare the title compound essentially as described in Example 1 using methyl 4-[[2-[4-[6-[(4-cyano-2-fluoro-phenyl)methoxy]-2-pyridyl]phenyl]acetyl]amino]-3-[[(2S)-oxetan-2-ylmethyl]amino]benzoate. Purify the crude product by reverse-phase flash chromatography using a gradient of 20 to 35% ACN in 5% aqueous $NH_4HCO_3$. ES/MS m/z 549.0 (M+H), 547.1 (M−H).

Biological Assays

Human GLP-1 Receptor HEK293 Cell cAMP Assay

GLP-1 Receptor functional activity is determined using cAMP formation in an HEK293 clonal cell line expressing human GLP-1R (NCBI accession number NP_002053) at an expression density of 581±94 (n=6) and 104±12 (n=5) fmol/mg protein (determined using [$^{125}$I]GLP-1(7-36)NH$_2$ homologous competition binding analysis). The hGLP-1R receptor expressing cells are treated with compound (20 point concentration-response curve in DMSO, 2.75-fold Labcyte Echo direct dilution, 384 well plate Corning Cat #3570) in DMEM (Gibco Cat #31053) supplemented with 1× GlutaMAX™ (Gibco Cat #35050), 0.1% bovine casein (Sigma C4765-10ML), 250 μM IBMX (3-Isobutyl-1-methylxanthine, Acros Cat #228420010) and 20 mM HEPES (Gibco Cat #15630) in a 20 μL assay volume (final DMSO concentration is 0.5%). After a 30 min incubation at 37° C., the resulting increase in intracellular cAMP is quantitatively determined using the CisBio cAMP Dynamic 2 HTRF Assay Kit (62AM4PEJ). Briefly, cAMP levels within the cell are detected by adding the cAMP-d2 conjugate in cell lysis buffer (10 μL) followed by the antibody anti-cAMP-Eu$^{3+}$-Cryptate, also in cell lysis buffer (10 μL). The resulting competitive assay is incubated for at least 60 min at RT, then detected using a PerkinElmer Envision® instrument with excitation at 320 nm and emission at 665 nm and 620 nm. Envision units (emission at 665 nm/620 nm*10,000) are inversely proportional to the amount of cAMP present and are converted to nM cAMP per well using a cAMP standard curve. The amount of cAMP generated (nM) in each well is converted to a percent of the maximal response observed with human GLP-1(7-36)NH$_2$. A relative $EC_{50}$ value and percent top ($E_{max}$) are derived by non-linear regression analysis using the percent maximal response vs. the concentration of compound added, fitted to a four-parameter logistic equation. The $EC_{50}$ and $E_{max}$ data when the compounds of Examples 1-6 are tested in the cAMP assay described above using HEK293 cells expressing 581 and 104 fmol/mg GLP-1R are shown in Tables 2 and 3, respectively. These data indicate that the compounds of Examples 1-6 are agonists of the human GLP-1 receptor.

TABLE 2

HEK293 cell line with 581 fmol/mg expression density of GLP-1R, intracellular cAMP response

| Example | $EC_{50}$ (nM) ± SEM (n) | $E_{max}$ (%) ± SEM (n) |
|---|---|---|
| 1 | 9.33 ± 1.36 (n = 6) | 99.5 ± 2.53 (n = 6) |
| 2 | 1.14 ± 0.315 (n = 6) | 104 ± 4.35 (n = 6) |
| 3 | 3.08 ± 0.379 (n = 5) | 99 ± 3.69 (n = 5) |
| 4 | 3.99 ± 0.378 (n = 3) | 99.2 ± 4 (n = 3) |
| 5 | 6.45 ± 0.934 (n = 3) | 105 ± 2.43 (n = 3) |
| 6 | 20 ± 6.51 (n = 4) | 101 ± 3.42 (n = 4) |

TABLE 3

HEK293 cell line with 104 fmol/mg expression density of GLP-1R, intracellular cAMP response

| Example | $EC_{50}$ (nM) ± SEM (n) | $E_{max}$ (%) ± SEM (n) |
|---|---|---|
| 1 | 20 ± 3.25 (n = 6) | 71.4 ± 2.26 (n = 6) |
| 2 | 3.97 ± 0.61 (n = 6) | 79.2 ± 3.2 (n = 6) |
| 3 | 10 ± 2.3 (n = 5) | 81.7 ± 3.86 (n = 5) |
| 4 | 9.59 ± 2.36 (n = 3) | 78.3 ± 5.1 (n = 3) |
| 5 | 23.6 ± 5.43 (n = 3) | 76.7 ± 3.88 (n = 3) |
| 6 | 47.7 ± 17.9 (n = 4) | 80.3 ± 3.1 (n = 4) |

In Vivo Intraperitoneal Glucose Tolerance Test in Human GLP-1R Knock-in Mice

The potency of the exemplified compounds to lower the concentration of blood glucose in vivo is determined using mice expressing the human GLP-1R (NCBI accession number NP_002053) from the mouse Glp-1r genetic locus (Jun, L. S., et al., PLoS One. 2014 9:e93746). Overnight fasted mice are orally administered the test compound solubilized in 10% Kolliphor® (HS15) in Polyetheylene Glycol 400 (PEG400). One hour post-dose, the animals are administered glucose by intraperitoneal injection (2 g/kg), and blood glucose levels are measured intermittingly over the next two hours using glucometers. A dose range of the test compound is delivered, and area under the curve calculations for each dose group are determined and fit to a four-parameter logistic model for calculating in vivo potency as an $ED_{50}$ with a 95% confidence interval. When tested in the in vivo intraperitoneal glucose tolerance test described above, the compounds of Examples 1-3 exhibit potency to lower the concentration of blood glucose in mice expressing the human GLP-1R with $ED_{50}$ (and 95% confidence interval) values as shown in Table 4, which indicates that these compounds are orally available potent GLP-1R agonists in mice.

TABLE 4

Blood glucose lowering efficacy in mice expressing human GLP-1R

| Example | Blood glucose lowering $ED_{50}$ (mg/kg) | 95% confidence interval |
|---|---|---|
| 1 | 0.09 | 0.0301-0.2592 |
| 2 | 0.07 | 0.0246-0.1808 |
| 3 | 0.06 | 0.013-0.246 |

Non-Human Primate (NHP) Pharmacokinetics:

The test compound is administered to fasted male cynomolgus monkeys intravenously (IV) at 0.5 mg/kg (using a dose volume of 1 mL/kg). Serial blood samples are collected at 0.08, 0.25, 0.5, 1, 2, 4, 8, 12, and 24 hours post dose for IV bolus. After treatment with an EDTA coagulant, plasma is obtained by centrifugation and stored at −70° C. until analysis by LC-MS/MS. Test article concentration is determined in plasma. Noncompartmental analysis is used to calculate plasma clearance and steady-state volume of distribution. Table 5 shows the pharmacokinetic data on the compounds of Examples 1-3 in this assay. These data, in part, are used to inform human mechanistic PK projections which suggest a human pharmacokinetic profile to support once daily dosing.

TABLE 5

Cynomolgous monkey pharmacokinetic data

| Example | Plasma clearance (mL/min/kg) | Volume of distribution (L/kg) | Vehicle* |
|---|---|---|---|
| 1 | 13 | 1.2 | A |
| 2 | 11 | 1.1 | A |
| 3 | 6 | 1.1 | B |

*Vehicle A—5% DMSO and 95% (20% CAPTISOL ® (w/v) in water;
Vehicle B—20% captisol (w/v) in water + 1 mole equivalent NaOH Phosphodiesterase 10 (PDE10) Enzyme Activity Assay To generate phosphodiesterase 10A1 (PDE10A1) protein, a full-length PDE10A1 clone corresponding to GenBank ID AAD32595.1 is cloned into pFastBac1 (Invitrogen). The PDE10A1 protein with a C-terminal FLAG-tag is expressed by baculoviral infection of insect cells and purified using anti-FLAG M2-agarose (Sigma) and size exclusion chromatography on a Superdex 200 column (GE Healthcare) and stored at −80° C. in small aliquots (20 mM Tris-HCl, Ph 7.5, 150 mM NaCl, 10% Glycerol).

PDE10A1 enzyme activities are measured with a yittrium silicate based scintillation proximity assay (SPA) that detects radioactive nucleotide monophosphates but not cyclic monophosphates. The assay buffer is composed of 50 mM Tris-HCl pH 7.5, 8 mM $MgCl_2$, 3.4 mM EDTA, and 0.1% BSA (Sigma). Assays are conducted in 384 well plates (3706, Corning) in a total volume of 50 μl: comprised of 24 μl PDE10A1 enzyme, 1 μl test compound and 25 μl of cyclic nucleotide. Test compounds are diluted in pure DMSO using ten-point concentration response curves with a 3-fold dilution factor and 1 μl is acoustically dispensed into assay plates using the Echo555 (LabCyte). 24 μl PDE10A1 protein is incubated with 1 μl compound for 30 min before the reaction is started by the addition of [8-$^3$H]-cGMP substrate (6.5 Ci/mmol, Perkin Elmer). Final concentration of components is 70 μM PDE10A1, 80 nM (3H-cGMP), and 2% DMSO in assay buffer. Maximal compound concentration in the reaction mixture is 10 μM. Reactions are incubated for 60 min at RT before quenching and the addition of 400 mg/per well SPA beads (RPNQ0150, Perkin Elmer). Bead bound radioactivity (product) is quantified 12 h later with a Microbeta counter (Perkin Elmer). Data is normalized to % inhibition and $IC_{50}$ values are calculated using the 4 parameter logistic equation as described (Campbell R. M.; Dymshitz, J.; Eastwood, B. J.; et al. "Data Standardization for Results Management." In: Sittampalam, G. S.; Grossman, A.; Brimacombe, K.; et al.; eds. *Assay Guidance Manual*. Bethesda (Md.): Eli Lilly & Company and the National Center for Advancing Translational Sciences; 2004.). Table 6 shows the activity of the compounds of Examples 1-4 in this assay. These data show that the compounds of Examples 1 to 4 have weak binding affinity to PDE10A, which indicates a reduced toxicity risk.

TABLE 6

In vitro potency for inhibition of PDE10A1

| Example | $IC_{50}$ (μM), n = 1 |
|---|---|
| 1 | >10 |
| 2 | 7.43 |
| 3 | >10 |
| 4 | 5.41 |

Human hERG $K^+$ Channel Affinity Radioligand Binding Assay

The affinity of compounds for the human hERG $K^+$ channel in transfected HEK-293 cells is evaluated in a radioligand binding assay as described herein. Cell membrane homogenates (about 40 g protein) are incubated for 60 min at 22° C. with 3 nM [$^3$H]dofetilide in the absence or presence of the test compound in a buffer containing 50 mM Tris-HCl (pH 7.4), 10 mM KCl and 1 mM $MgCl_2$. The assay is carried out in a 96-well plate format with a volume of 200 μL, containing a maximum of 1% DMSO from initial solubilization of test compound. Following incubation, the samples are filtered rapidly under vacuum through glass fiber filters (GF/B, Packard) presoaked with 0.3% PEI and rinsed several times with ice-cold 50 mM Tris-HCl, 10 mM KCl and 1 mM $MgCl_2$ using a 96-sample cell harvester (Unifilter, Packard). The filters are dried and then counted for radioactivity in a scintillation counter (Topcount, Packard) using a scintillation cocktail (Microscint 0, Packard). Table 7 shows the activity of Examples 1-3 in this assay, expressed as a percent inhibition of the control radioligand specific binding. These data show that the compounds of Examples 1 to 3 have weak hERG inhibitory activity, which indicates a reduced toxicity risk.

TABLE 7

Human hERG K+ channel affinity radioligand percent inhibition

| Example | Percent inhibition (%) at 100 μM compound concentration, n = 1 |
|---------|---------------------------------------------------------------|
| 1 | 0 |
| 2 | 54 |
| 3 | 37 |

The invention claimed is:

1. A compound of the formula:

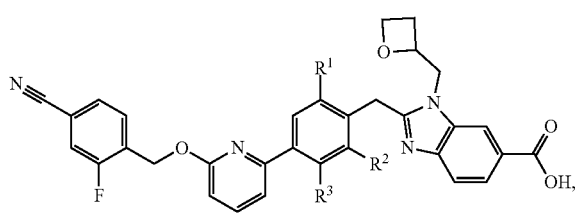

wherein
$R^1$ is H or F;
$R^2$ is H; and
$R^3$ is $CH_3$;
or a pharmaceutically acceptable salt thereof.

2. The compound according to claim 1, wherein the compound is of the formula:

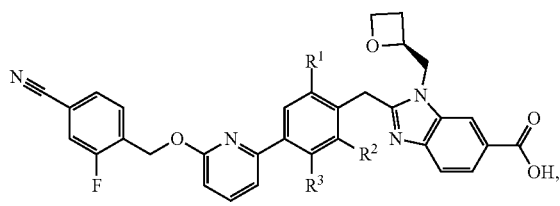

or a pharmaceutically acceptable salt thereof.

3. The compound according to claim 1, wherein the compound is:

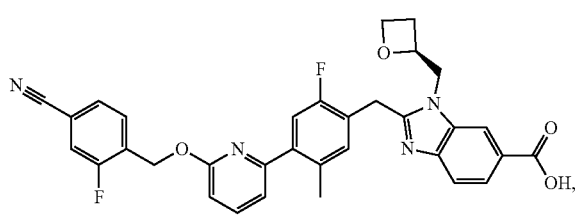 [SMILES: Cc1cc(Cc2nc3ccc(C(=O)O)cc3n2C[C@@H]2CCO2)c(F)cc1-c1cccc(OCc2ccc(C#N)cc2F)n1]

or a pharmaceutically acceptable salt thereof.

4. The compound according to claim 3, which is the tert-butylamine salt of:

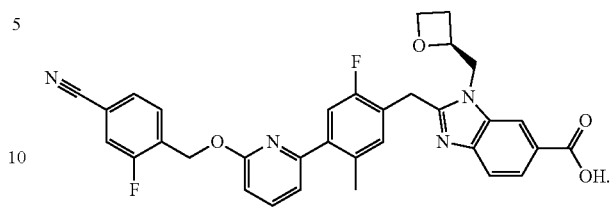

5. A pharmaceutical composition comprising a compound, or a pharmaceutically acceptable salt thereof, according to claim 1 and at least one pharmaceutically acceptable carrier, diluent, or excipient.

6. A pharmaceutical composition comprising a compound, or a pharmaceutically acceptable salt thereof, according to claim 3 and at least one pharmaceutically acceptable carrier, diluent, or excipient.

7. A method of treating type II diabetes mellitus in a mammal comprising administering to the mammal an effective amount of a compound according to claim 1, or a pharmaceutically acceptable salt thereof.

8. The method according to claim 7, wherein the compound is administered orally.

9. A method of lowering blood glucose levels in a mammal comprising administering to the mammal an effective amount of a compound according to claim 1, or a pharmaceutically acceptable salt thereof.

10. The method according to claim 9, wherein the compound is administered orally.

11. A method of treating hyperglycemia in a mammal comprising administering to the mammal an effective amount of a compound according to claim 1, or a pharmaceutically acceptable salt thereof.

12. The method according to claim 11, wherein the compound is administered orally.

13. A method of treating type II diabetes mellitus in a mammal comprising administering to the mammal an effective amount of a compound according to claim 3, or a pharmaceutically acceptable salt thereof.

14. The method according to claim 13, wherein the compound is administered orally.

15. A method of lowering blood glucose levels in a mammal comprising administering to the mammal an effective amount of a compound according to claim 3, or a pharmaceutically acceptable salt thereof.

16. The method according to claim 15, wherein the compound is administered orally.

17. A method of treating hyperglycemia in a mammal comprising administering to the mammal an effective amount of a compound according to claim 3, or a pharmaceutically acceptable salt thereof.

18. The method according to claim 17, wherein the compound is administered orally.

* * * * *